(12) United States Patent
Schappacher-Tilp et al.

(10) Patent No.: US 11,450,405 B2
(45) Date of Patent: Sep. 20, 2022

(54) TECHNIQUES FOR MODELING PARATHYROID GLAND FUNCTIONALITY AND CALCIMIMETIC DRUG ACTIVITY

(71) Applicant: Fresenius Medical Care Holdings, Inc., Waltham, MA (US)

(72) Inventors: Gudrun Schappacher-Tilp, Graz (AT); Peter Kotanko, New York, NY (US); Doris Helen Fuertinger, Frankfurt am Main (DE)

(73) Assignees: Fresenius Medical Care Holdings, Inc., Waltham, MA (US); FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 250 days.

(21) Appl. No.: 16/655,873

(22) Filed: Oct. 17, 2019

(65) Prior Publication Data
US 2020/0126632 A1     Apr. 23, 2020

Related U.S. Application Data

(60) Provisional application No. 62/747,540, filed on Oct. 18, 2018.

(51) Int. Cl.
*G16B 5/00*        (2019.01)
*G06F 30/20*      (2020.01)
(Continued)

(52) U.S. Cl.
CPC .............. *G16B 5/00* (2019.02); *G06F 30/20* (2020.01); *G06F 17/16* (2013.01); *G06F 2111/10* (2020.01)

(58) Field of Classification Search
CPC . G16B 5/00; G06F 30/20; G06F 17/16; G06F 2111/10
(Continued)

(56) References Cited

U.S. PATENT DOCUMENTS

2017/0046477 A1*   2/2017   Van Ooijen .............. G16B 5/20

OTHER PUBLICATIONS

Leach et al. "Towards a structural understanding of allosteric drugs at the human calcium-sensing receptor," Cell Research 26:574-592, 2016.
(Continued)

*Primary Examiner* — Brian S Cook
(74) *Attorney, Agent, or Firm* — KDB

(57) ABSTRACT

The described technology may include processes to model parathyroid gland (PTG) functionality and/or calcimimetic administration to patients with a health abnormality that affects PTG function. In one embodiment, a method may include providing a PTG functionality model configured to simulate functionality of a PTG of a patient with a health abnormality affecting PTG function, the model may receive a parameters configured to regulate activity of calcium-sensing receptors (CaSR), the parameters may include a calcium concentration, a vitamin D concentration, and a phosphorous concentration, simulate CaSR expression and vitamin D receptor (VDR) expression via a positive feedback loop between the CaSR expression and the VDR expression, and suppression of the CaSR expression and the VDR expression by P, initiate at least one PTG adaptation based on the parameters, and determine a model output comprising a parathyroid hormone (PTH) concentration at one or more time intervals. Other embodiments are described.

18 Claims, 23 Drawing Sheets

(51) Int. Cl.
G06F 111/10 (2020.01)
G06F 17/16 (2006.01)
(58) Field of Classification Search
USPC .......................................................... 703/2
See application file for complete search history.

(56) References Cited

OTHER PUBLICATIONS

Leach et al., "Molecular Mechanisms of Action and In Vivo Validation of an M-4 Muscarinic Acetylcholine Receptor Allosteric Modulator with Potential Antipsychotic Properties," Neuropsychopharmacology 35:855-869, 2010.
Leach et al., "Allosteric GPCR modulators: taking advantage of permissive receptor pharmacology," Trends in Pharmacological Sciences 28:382-389, 2007.
Padhi et al., "Clinical Pharmacokinetic and Pharmacodynamic Profile of Cinacalcet Hydrochloride," Clinical Pharmacokinetics 48:303-311, 2009.
KDIGO 2017 Clinical Guideline Update for the Diagnosis, Evaluation, Prevention, and Treatment of Chronic Kidney Disease-Mineral and Bone Disorder (CKD-MBD', (2017), Kidney International Supplements, J. Intl. Soc. Neph. 7(1), Jul. 2017.
Ben-Dov, I.Z. et al. "The Parathyroid is a Target Organ for FGF23 in Rats", J Clin Invest 117(12):4003-4008 (2007).
Benzekry, S. et al. "Classical Mathematical Models for Description and Prediction of Experimental Tumor Growth", PLoS Comput Biol 10(8): e1003800 (2014).
Block, G.A. et al. "Cinacalcet for Secondary Hyperparathyroidism in Patients Receiving Hemodialysis", N Engl J Med 350:1516-1525 (2004).
Block, G.A. et al. "Re-evaluation of Risks Associated with Hyperphosphatemia and Hyperparathyroidism in Dialysis Patients: Recommendations for a Change in Management", Am. J Kidney Disease 35(6):1226-1237 (2000) (Abstract).
Borrego, M.J. et al. "Evidence for Adaptation of the Entire PTH-calcium Curve to Sustained Changes in the Serum Calcium in Haemodialysis Patients", Nephrol Dial Transplantation 12:505-513 (1997).
Brent, G.A. et al. "Relationship Between the Concentration and Rate of Change of Calcium and Serum Intact Parathyroid-Hormone Levels in Normal Humans", J Clin Endocrinol Metab 67(5):944-950 (1988).
Brown, E.M. et al. "4-parameter Model of the Sigmoidal Relationship Between Parathyroid-Hormone Release and Extracellular Calcium-Concentration in normal and Abnormal Parathyroid Tissue", J Clin Endocrinol Metab 56 (3):572-581 (1983) (Abstract).
Brown, E.M. et al. "The Acute Secretory Response to Alterations in Extracellular Calcium Concentration and Dopamine in Perifused Bovine Parathyroid Cells", Endocrinol 116(3):1123-1132 (1985) (Abstract).
Brown, E.M. "Clinical Lessons from the Calcium-Sensing Receptor", Nat Clin Practice Endocrinol and Metab 3, 122-133 (2007) (Abstract).
Brown, E.M. "Control of Parathyroid Hormone Secretion by Its Key Physiological Regulators". In the Parathyroids Basic and Clinical Concepts, edited by Bilezikian, J, 101-118 Elsevier, 2015 (Abstract).
Brown, A.J. et al. "Decreased Calcium-Sensing Receptor Expression in Hyperplastic Parathyroid Glands of Uremic Rats: Role of Dietary Phosphate", Kid Int 55:1284-1292 (1999).
Canalejo, A. et al. "The In Vitro Effect of Calcitriol on Parathyroid Cell Proliferation and Apoptosis", J Am Soc Nephrol 11:1865-1872 (2000).
Chakravarti, B. et al. "In Calcium Signaling", edited by Islam, MS, vol. 740, 103-142. Advances in Experimental Medicine and Biology, 2012 (Abstract).
Chen, R.A. et al. "Role of the Calcium-Sensing Receptor in Parathyroid Gland Physiology", Am J Physiol Renal Physio 286:F1005-F1011 (2004).

Cheung, A.K. et al. "Atherosclerotic Cardiovascular Disease Risks in Chronic Hemodialysis Patients", Kid Int 58: 353-362 (2000).
Christie, C.R. et al. "A Control Engineering Model of Calcium Regulation", J Clin Endocrinol Metab 99(8):2844-2853 (2014).
Conigrave, A.D. et al. "Calcium-Sensing Receptor (CaSR): Pharmacological Properties and Signaling Pathways", Best Practice & Research Clin Endocrinol & Metab 27(3):315-331 (2013) (Abstract).
Conlin, P.R. et al. "Hysteresis in the Relationship Between Serum Ionized Calcium and Intact Parathyroid-Hormone During Recovery from Induced Hypercalcemia and Hypocalcemia in Normal Humans", J Clin Endocrinol Metab 69 (3):593-599 (1989).
Denda, M. et al. "Phosphorus Accelerates the Development of Parathyroid Hyperplasia and Secondary Hyperparathyroidism in Rats with Renal Failure", Am J Kidney Diseases 28(4):596-602 (1996) (Abstract).
Dong, B.J. "Cinacalcet: An Oral Calcimimetic Agent for the Management of Hyperparathyroidism", Clin. 27 (11):1725-1751 (2005) Abstract.
Estepa, J.C. et al. "Effect of Rate of Calcium Reduction and a Hypocalcemic Clamp on PTH Secretion: A Study in dogs", Kid Int 55:1724-1733 (1999).
Food & Administration, D. Sensipar™ (Cinacalcet HCI) FDA (2004). URL https://www.accessdata.fda.gov/drugsatfda_docs/nda/2004/21-688.pdf_Sensipar_Pharmr_P1.pdf.
Felsenfeld, A.J. et al. "Dynamics of Parathyroid Hormone Secretion in Health and Secondary Hyperparathyroidism", Clin J Am Soc Nephrol 2:1283-1305 (2007).
Fukagawa, M. et al. "Basic and Clinical Aspects of Parathyroid Hyperplasia in Chronic Kidney Disease", Kid Int 70:S3-S7, 2006.
Fukagawa, M. et al. "Regression of Parathyroid Hyperplasia by Calcitriol-Pulse Therapy in Patients on Long-Term Dialysis", N Engl J Med 323:421-422 (1990) (Abstract).
Gincherman, Y. et al. "Assessment of Adherence to Cinacalcet by Prescription Refill Rates in Hemodialysis Patients", Hemodialysis International 14(1):68-72 (2010) (Abstract).
Gogusev, J. et al. "Depressed Expression of Calcium Receptor in Parathyroid Gland Tissue of Patients with Hyperparathyroidism", Kid Int 51:328-336 (1997).
Gonzalez, E.A. et al. "Vitamin D Insufficiency and Deficiency in Chronic Kidney Disease—A Single Center Dbservational Study", Am J Nephrol 24:503-510 (2004) (Abstract).
Goodman, W.G. et al. "Calcium-Sensing by Parathyroid Glands in Secondary Hyperparathyroidism", J Clin Endocrinol Metab 83(8):2765-2772 (1998).
Goodman, W.G. et al. "Development and Progression of Secondary Hyperparathyroidism in Chronic Kidney Disease Lessons from Molecular Genetics", Kid Int 74:276-288 (2008).
Graciolli, F.G. et al. "The Complexity of Chronic Kidney Disease-Mineral and Bone Disorder Across Stages of Chronic Kidney Disease", Kid Int 91(6):1436-1446 (2017) (Abstract).
Granjon, D. et al. "Coupling Between Phosphate and Calcium Homeostasis: A Mathematical Model", Am J Physiol Renal Physiol 313:F1181-F1199 (2017).
Grant, F.D. et al. "Rate and Concentration Dependence of Parathyroid Hormone Dynamics During Stepwise Changes in Serum Ionized Calcium in Normal Humans", J Clin Endocrinol Metab 71(2):370-378 (1990) (Abstact).
Gutierrez, O. et al. "Fibroblast Growth Factor-23 Mitigates Hyperphosphatemia but Accentuates Calcitriol Deficiency in Chronic Kidney Disease", J Am Soc Nephrol 16:2205-2215 (2005).
Habener, J.F. "Regulation of Parathyroid Hormone Secretion and Biosynthesis", Ann Rev Physiol 43:211-223 (1981).
Harris, R.Z. et al. "Pharmacokinetics, Pharmacodynamics, and Safety of Cinacalcet Hydrochloride in Hemodialysis Patients at Doses Up To 200 mg Once Daily", Am J Kid Dis 44(6):1070-1076 (2004) (Abstract).
Isakova, T. et al. "Fibroblast Growth Factor 23 and Incident CKD in Type 2 Diabetes", Clin J Am Soc Nephrol 10:29-38 (2015).
Isakova, T. et al. "Fibroblast Growth Factor 23 and Risks of Mortality and End-Stage Renal Disease in Patients with Chronic Kidney Disease", JAMA—J Am Med Assoc 305(23):2432-2439 (2011).

(56) References Cited

OTHER PUBLICATIONS

Jadoul, M. et al. "Incidence and Risk Factors for Hip or other Bone Fractures Among Hemodialysis Patients in the Dialysis Outcomes and Practice Patterns Study", Kid Int 70:1358-1366 (2006).
Jueppner, H. et al. "FGF-23: More than a Regulator of Renal Phosphate Handling?", J Bone Min Res 25 (10):2091-2097 (2010).
Kawata, T. et al. "Parathyroid Hormone Regulates Fibroblast Growth Factor-23 in a Mouse Model of Primary Hyperparathyroidism", J Am Soc Nephrol 18:2683-2688 (2007).
Ketteler, M. et al. "Executive Summary of the 2017 KDIGO Chronic Kidney Disease-Mineral and Bone Disorder (CKD-MBD) Guideline Update: What's Changed and Why it Matters", Kid Int 92:26-36 (2017).
Komaba, H. et al. "The Role of FGF23 in CKD-with or without Klotho", Nat Rev Nephrol 8:484-490 (2012) (Abstract).
Kroll, M. "Parathyroid Hormone Temporal Effects on Bone Formation and Resorption", Bulletin of Mathematical Biology 32:163-188 (2000) (Abstract).
Kumar, G.N. et al. "Metabolism and Disposition of Calcimimetic Agent Cinacalcet HCL in Humans and Animal Models" Drug Metab and Disposition 32(12):1491-1500 (2004) (Abstract).
Leach, K. et al. "Allosteric GPCR Modulators: Taking Advantage of Permissive Receptor Pharmacology", Trends in Pharmacological Sciences 28(8):382-389 (2007) (Abstract).
Leach, K. et al. "Molecular Mechanisms of Action and In Vivo Validation of an M4 Muscarinic Acetylcholine Receptor Allosteric Modulator with Potential Antipsychotic Properties" Neuropsychopharmacol 35:855-869 (2010).
Leach, K. et al. "Towards a Structural Understanding of Allosteric Drugs at the Human Calcium-Sensing Receptor", Cell Res 26:574-592 (2016).
Lemaire, V. et al. "Modeling the Interactions Between Osteoblast and Osteoclast Activities in Bone Remodeling" J Theoretical Biol 229(3):293-309 (2004) Abstract.
Levin, A. et al. "Prevalence of Abnormal Serum Vitamin D, PTH, Calcium, and Phosphorus in Patients with Chronic Kidney Disease: Results of the Study to Evaluate Early Kidney Disease", Kid Int 71:31-38 (2007).
Riggs, M.M., et al., "Multiscale physiology-based modeling of mineral bone disorder in patients with impaired kidney function" J. Clin. Pharmacol. 52:45S-53S (2012) Abstract.
Wang, M.D., et al., "Stretching DNA with optical tweezers", Biophys. J. 72:1335-1346 (1997).
Liu, S. et al. "Fibroblast Growth Factor 23 Is a Counter-Regulatory Phosphaturic Hormone for Vitamin D", J Am Soc Nephrol 17:1305-1315 (2006).
Mace, M. L. et al. "Fibroblast Growth Factor (FGF) 23 Regulates the Plasma Levels of Parathyroid Hormone In Vivo Through the FGF Receptor in Normocalcemia, But Not in Hypocalcemia", Calcif Tissue Int 102:85-92 (2018).
Martin, K.J. et al. "Metabolic Bone Disease in Chronic Kidney Disease", J Am Soc Nephrol 18, 875-885 (2007) Abstract.
Melamed, M.L. et al. "Changes in Serum Calcium, Phosphate, and PTH and the Risk of Death in Incident Dialysis Patients: A Longitudinal Study", Kid Int 70:351-357 (2006).
Messa, P. et al. "Direct In-Vivo Assessment of Parathyroid Hormone-Calcium Relationship Curve in Renal Patients", Kid Int 46:1713-1720 (1994).
Moallem E. et al. "RNA-Protein Binding and Post-Transcriptional Regulation of Parathyroid Hormone Gene Expression by Calcium and Phosphate", J Biol Chem 273(9):5253-5259 (1998).
Moe, S.M. et al. "Achieving NKF-K/DOQI™ Bone Metabolism and Disease Treatment Goals with Cinacalcet HCl", Kid Int 67:760-771 (2005).
Moe, S. et al. "Definition, Evaluation, and Classification of Renal Osteodystrophy: A Position Statement from Kidney Disease: Improving Global Outcomes (KDIGO)", Kid Int 69:1945-1953 (2006).

Momsen, G. et al. "A Mathematical/Physiological Model of Parathyroid Hormone Secretion in Response to blood-onized Calcium Lowering In Vivo", Scandinavian J Clin Lab Invest 57:381-394 (1997) (Abstract).
Naveh-Many, T. et al. "Parathyroid Cell Proliferation in Normal and Chronic Renal Failure Rats—the Effect of Calcium Phosphate, and Vitamin-D", J Clin Invest 96:1786-1793 (1995).
Nemeth, E.F. "Pharmacological Regulation of Parathyroid Hormone Secretion", Curr Pharm Des 8(23):2077-2087 (2002) (Abstract).
Nickolas, T.L. et al. "Chronic Kidney Disease and Bone Fracture: A Growing Concern", Kid Int 74:721-731 (2008).
Padhi, D. et al. "Clinical Pharmacokinetic and Pharmacodynamic Profile of Cinacalcet Hydrochloride", Clin Pharmaco 48:303-311 (2009) (Abstract).
Padhi, D. et al. "The Pharmacokinetics of Cinacalcet are Unaffected Following Consumption of High- and Low-Fat Meals", Am J Ther 14(3):235-240 (2007) (Abstract).
Padhi, D. et al. "Pharmacokinetics and Pharmacodynamics of Cinacalcet in Hepatic Impairment", Clin Drug Invest 28:635-643 (2008) (Abstract).
Palmer, S.C. et al. "Serum Levels of Phosphorus, Parathyroid Hormone, and Calcium and Risks of Death and Cardiovascular Disease in Individuals with Chronic Kidney Disease", JAMA—J Am Med Assoc 305(11):1119-1127 (2011).
Peterson, M.C. et al. "A Physiologically Based Mathematical Model of Integrated Calcium Homeostasis and Bone Remodeling", Bone 46(1):49-63 (2010) (Abstract).
Pocotte, S.L. et al. "Regulation of Parathyroid Hormone Secretion", Endocrine Rev 12(3):291-301 (1991) (Abstract).
Quarles, L.D. et al. "Prospective Trail of Pulse Oral Versus Intravenous Calcitriol Treatment of Hyperparathyroidism in ESRD", Kid Int 45:1710-1721 (1994).
Quarles, L.D. et al. "Skeletal Secretion of FGF-23 Regulates Phosphate and Vitamin D Metabolism", Nat Rev Endocrinol 8(5):276-286 (2012).
Raggi, P. et al. "Cardiac Calcification in Adult Hemodialysis Patients—A link Between End-Stage Renal Disease and Cardiovascular Disease?", J Am Coll Cardiol 39(4):695-701 (2002).
Raposo, J.F. et al. "A Mathematical Model of Calcium and Phosphorus Metabolism in Two Forms of Hyperparathyroidism", Endocrine 41:309-319 (2012).
Raposo, J.F. et al. "A Minimal Mathematical Model of Calcium Homeostasis", J Clin Endocrinol Metab 87(9):4330-4340 (2002).
Ribba, B. et al. "A model of Vascular Tumour Growth in Mice Combining Longitudinal Tumour Size Data with Histological Biomarkers", Eur J Can 47:479-490 (2011).
Roche, D. et al. "Mechanistic Analysis of the Function of Agonists and Allosteric Modulators: Reconciling Two-State and Operational Models", British J of Pharmaco 169:1189-1202 (2013).
Rutherford, W. E. et al. "Phosphate Control and 25-Hydroxycholecalciferol Administration in Preventing Experimental Renal Osteodystrophy in the Dog", J Clin Invest 60:332-341 (1977).
Schmitt, C.P. et al. "Calcium Sensitivity of the Parathyroid in Renal Failure: Another Look with New Methodology", Nephrol Dial Transplant 14:2815-2818 (1999).
Schmitt, C.P. et al. "Control of Pulsatile and Tonic Parathyroid Hormone Secretion by Ionized Calcium", J Clin Endocrinol Metab 81:4236-4243 (1996).
Schwarz, P. et al. "Cica-Clamp Technique: A Method for Quantifying Parathyroid Hormone Secretion: A Sequential Citrate and Calcium Clamp Study", Eur J Clin Invest 23(9):546-553 (1993.
Schwarz, P. et al. "Evidence for a Role of Intracellular Stored Parathyroid Hormone in Producing Hysteresis of the PTH-calcium Relationship in Normal Humans", Clin Endocrinol 48(6):725-732 (1998) Abstract.
Shimada, T. et al. "Cloning and Characterization of FGF23 as a Causative Factor of Tumor-Induced Osteomalacia", Pros Nat Acad Sci 98(11):6500-6505 (2001).
Shimada, T. et al. "FGF-23 is a Potent Regulator of Vitamin D Metabolism and Phosphate Homeostasis", J Bone Miner Res 19(3):429-435 (2004).

(56) References Cited

OTHER PUBLICATIONS

Shrestha, R.P. et al. "A Mathematical Model of Parathyroid Hormone Response to Acute Changes in Plasma Ionized Calcium Concentration in Humans", Mathematical Biosciences 226:46-57 (2010).

Silver, J. et al. "New Insights into the Regulation of Parathyroid Hormone Synthesis and Secretion in Chronic Renal Failure", Nephrol Dial Transplant 11(3):2-5 (1996).

Silver, J. et al. "Phosphate and the Parathyroid", Kid Int 75:898-905 (2009).

Slatopolsky, E. et al. "The Role of Phosphorus in the Development of Secondary Hyperparathyroidism and Parathyroid Cell Proliferation in Chronic Renal Failure", Am J Med Sci 317(6):370-376 (1999) (Abstract).

Stehman-Breen, C.O. et al. "Risk Factors for Hip Fracture Among Patients with End-Stage Renal Disease", Kid Int 58:2200-2205 (2000).

Takahashi, F. et al. "Hyperplasia of the Parathyroid Gland without Secondary Hyperparathyroidism", Kid Int 51:1332-1338 (2002).

Teng, M. et al. "Survival of Patients Undergoing Hemodialysis with Paricalcitol or Calcitriol Therapy", N Engl J Med 349 (5):446-456 (2003).

Tokumoto, M. et al. "Parathyroid Cell Growth in Patients with Advanced Secondary Hyperparathyroidism: Vitamin D Receptor, Calcium Sensing Receptor, and Cell Cycle Regulating Factors", Ther Apher Dial 9(s1):S27-S34 (2005) (Abstract).

Valle, C. et al. "Cinacalcet Reduces the Set Point of the PTH-Calcium Curve", J Am Soc Nephrol 19:2430-2436 (2008).

Vervloet, M.G. et al. "The Role of Phosphate in Kidney Disease", Nat Rev Nephrol 13:27-38 (2017) (Abstract).

Wang, Q. et al. "The Basal Rate of Cell Proliferation in Normal Human Parathyroid Tissue: Implications for the Pathogenesis of Hyperparathyroidism", Clin Endocrinol 46(3):343-349 (1997) (Abstract).

White, K.E. et al. "Autosomal Dominant Hypophosphataemic Rickets is Associated with Mutations in FGF23", Nat Gen 26:345-348 (2000) (Abstract).

Schappacher-Tilp et al., "A Multi-Compartment Model Capturing the Pharmacokinetics of the Calcimimetic Cinacalcet", Cell Physiol Biochem 53:429-438 (2019) Abstract.

Schappacher-Tilp et al., "A Mathematical Model of Parathyroid Gland Biology", Physiol Rep 7(7):e14042, 1-15 (2019).

Brea, J., et al., "Evidence for distinct antagonist-revealed functional states of 5-hydroxytryptamine(2A) receptor homodimers" Mol. Pharmacol. 75:1380-1391 (2009).

Drueke, T.D., et al., "Can calcimimetics inhibit parathyroid hyperplasia? Evidence from preclincial studies", Nephrol. Dial Transplant 22:1828-1839 (2007).

Jean, G.C., et al., "Six cases of successful cinacalcet cessation in haemodialysis patients treated for secondary hyperparathyroidism", Nephrol. Dial Transplant 22:2102-2103 (2007).

Meola, M., et al., "Long-term treatment with cinacalcet and conventional therapy reduces parathyroid hyperplasia in severe secondary hyperparathyroidism", Nephrol. Dial Transplant. 24:982-989 (2009).

\* cited by examiner

505

| Compartment | Parameter | Value | Source |
|---|---|---|---|
| PTG | $k_{sq}$ | $2 \cdot 10^{-3}$ /min | [Reference 56] |
|  | $k_{qs}$ | $5 \cdot 10^{-4}$ min$^{-1}$ | [Reference 56] |
|  | $k_p^q$ | $3 \cdot 10^{-3}$ /min | [Reference 77] |
|  | $k_o$ | 0.001 min$^{-1}$ | [Reference 77] |
| PTH release | $A$ | 0.12 pmol/min | [Reference 67] |
|  | $B$ | 0.001 pmol/min | [Reference 67] |
|  | $S_c$ | 1.1881 mmol/L | [Reference 67] |
|  | $m$ | 50 | [Reference 67] |
| Clearance | $k_c$ | 0.632/min | [Reference 67] |
| Degradation | $A_d^p$ | 0.012/min | [Reference 67] |
| Production | $A_{pr}$ | 132 | [Reference 67] |
| Proliferation | $A_p$ | 0.003/min | [Reference 19] |
|  | $k_p$ | $5 \cdot 10^{-4}$ |  |

*FIG. 5*

| Compartment | Parameter | Value |
|---|---|---|
| Optimal Values | $C$ | 5 mg/dl |
| | $P$ | 4.5 mg/dl |
| | $D$ | 45 pg/ml |
| Stimulus | $C_1$ | 2 mg/dl |
| | $K_C$ | 2 dl/mg |
| | $D_1$ | 45 ng/ml |
| | $K_D$ | 0.2 ml/ng |
| | $P_1$ | 2.5 mg/dl |
| | $K_P$ | 2.5 dl/mg |

| Compartment | Parameter | Value |
|---|---|---|
| Degradation | $\tau_{Ca}$ | $10^{-3}$ |
| | $\tau_P$ | $5 \cdot 10^{-3}$ |
| | $p_{Ca}$ | 25 |
| | $n_{Ca}$ | 0.5 |
| Production | $\tau_{Ca}$ | $10^{-3}$ |
| | $\tau_P$ | $10^{-4}$ |
| | $p_{Ca}$ | 25 |
| | $n_{Ca}$ | 0.5 |
| Proliferation | $\tau_{Ca}$ | $5 \cdot 10^{-3}$ |
| | $\tau_P$ | $5 \cdot 10^{-4}$ |
| | $p_{Ca}$ | 25 |
| | $n_{Ca}$ | 0.5 |
| Expression | $\tau_{Ca}$ | $10^{-4}$ |
| | $\tau_P$ | $10^{-1}$ |
| | $\tau_D$ | $10^{-4}$ |
| | $p_{Ca}$ | $5 \cdot 10^{-3}$ |
| | $n_{Ca}$ | $5 \cdot 10^{-3}$ |
| | $p_D$ | $5 \cdot 10^{-7}$ |
| | $n_D$ | $5 \cdot 10^{-7}$ |

*FIG. 7*

| | 1905 |
|---|---|
| $k_a$ | $0.4\ h^{-1}$ |
| $k_e$ | $0.266\ h^{-1}$ |
| $k_{lp}$ | $0.09\ h^{-1}$ |
| $k_e^p$ | $130\ h^{-1}$ |
| $k_b$ | $1 \cdot 10^3\ h^{-1}$ |
| $k_{PTf}$ | $550\ h^{-1}$ |
| $k_{TPf}$ | $0.08\ h^{-1}$ |
| $k_{PTs}$ | $50\ h^{-1}$ |
| $k_{TPs}$ | $1 \cdot 10^{-5}\ h^{-1}$ |

*FIG. 19*

| Parameter | $C_{max}$ | $t_{max}$ | Bio | $t_{1/2}$ | $t'_{1/2}$ | VD | CL/F |
|---|---|---|---|---|---|---|---|
| Base line | 25.6 ng/ml | 3.1 h | 22.8% | 35.2 h | 6 h | 1056 L | 33 L/h |
| $k_e$, -0.5/2 | -7.1/7.5 ng/dl | 1.6/-1.1 h | 0/0 % | -0.3/0 h | 5.0/-2 h | 62.6/-32.9 L | 0/0 L/h |
| $k_a$, -0.5/2 | 6.9/-7.1 ng/dl | 0.9/-0.9 H | 13.6/-9.7 % | -0.1/0 h | 3.2/-1.9 h | 36.6/-73.4 L | -20.6/69.6 L/h |
| $k'_a$, -0.5/2 | -11.9/19.5 ng/dl | 0.3/-0.4 h | -9.7/13.6 % | 0/0 h | 0.7/-0.9 h | 80.7/-40.3 L | 0/0 L/h |
| $k'_e$, -0.5/2 | 1/-1.8 ng/dl | 0/0 h | 0/0 % | 4.2/-5.8 h | 0.2/-0.3 h | 19.2/-27.3 L | 69.8/-23.6 L/h |
| $k_{PT,f}$, -0.5/2 | 0/0 ng/dl | 0/0 h | 0/0 % | 0/0 h | 0/0 h | 0.5/-0.3 L | 0/0 L/h |
| $k_{TP,f}$, -0.5/2 | -1.5/3.3 ng/dl | -0.3/0.6 h | 0/0 % | 35.2/-17.6 h | -1.4/0 h | -17.5/13.1 L | 0/0 L/h |
| $k_{PT,s}$, -0.5/2 | 14.4/-10.7 ng/dl | -0.1/0 h | 0/0 % | -13.3/26.5 h | -0.8/0.8 h | -20.8/-27 L | 0/0 L/h |
| $k_{TP,s}$, -0.5/2 | 0/0 ng/dl | 0/0 h | 0/0 % | 0/0 h | 0/0 h | 0/0 L | 0/0 L/h |

TECHNIQUES FOR MODELING PARATHYROID GLAND FUNCTIONALITY AND CALCIMIMETIC DRUG ACTIVITY

CROSS-REFERENCE TO RELATED APPLICATION

This application claims priority to U.S. Provisional Patent Application Ser. No. 62/747,540, filed on Oct. 18, 2018, entitled "Models, Multi-Compartment Models, and Techniques for Modeling Pharmacokinetics of the Calcimimetic Cinacalcet," the contents of which are incorporated herein by reference.

FIELD

The disclosure generally relates to processes for modeling the functionality of portions of the human body to generate healthcare recommendations and, more particularly, to techniques for modeling parathyroid gland (PTG) functionality and the activity of calcimimetic compounds.

BACKGROUND

The concentration of extracellular ionized calcium is maintained within a narrow physiologic range via a biological system of negative and positive feedback regulators involving the major organs that transport calcium and phosphate, including the intestine, kidneys, bones, and the endocrine glands with the parathyroid gland (PTG) as the most prominent regulator. In patients with certain abnormal health conditions, such as chronic kidney disease (CKD) the loss of the regulatory kidney function triggers a cascade of processes eventually leading to disruptions to the ionized calcium regulatory system and associated health conditions, such as secondary hyperparathyroidism.

Clinical studies are an important tool for understanding the ionized calcium regulatory system in patients, particularly those with abnormal health conditions. However, clinical studies are expensive, time-consuming, and resource-intensive. Accordingly, virtual models of biological systems, such as the PTG, may be used in some situations to evaluate functionality and treatments without the need for real-world patients, regulations, and cost. In addition, virtual models may provide a wealth of biological information on a small time scale. Although some conventional models have been described for modeling PTG functionality, such modeling is limited. For example, conventional models do not accurately reflect PTG functionality in patient populations with health abnormalities that effect the PTG, such as CKD.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In accordance with various aspects of the described embodiments, a computer-implemented method of virtual parathyroid gland (PTG) functionality analysis may include, via a processor of a computing device, providing a PTG functionality model configured to simulate a functionality of a PTG of a patient with at least one health abnormality affecting PTG function, the model may be operative to receive a plurality of parameters configured to regulate activity of calcium-sensing receptors (CaSR), the plurality of parameters may include a calcium concentration, a vitamin D concentration, and a phosphorous concentration, simulate CaSR expression and vitamin D receptor (VDR) expression via a positive feedback loop between the CaSR expression and the VDR expression, and suppression of the CaSR expression and the VDR expression by P, initiate at least one PTG adaptation based on the plurality of parameters, and determine a model output that may include a parathyroid hormone (PTH) concentration at one or more time intervals.

In some embodiments of the method, the at least one health abnormality may include one of chronic kidney disease (CKD), hypoparathyroidism, hyperparathyroidism, hypocalcemia, hypercalcemia or hyperphosphatemia. In various embodiments of the method, the model may be operative to down-regulate at last one of a PTH release rate, a production rate, or a proliferation rate responsive to the calcium concentration, the vitamin D concentration, and the phosphorous concentration being within an optimal range. In some embodiments of the method, the model may be operative to initiate the at least one PTG adaptation responsive to one of the plurality of parameters being outside of an optimal range for a critical time period. In various embodiments of the method, the calcium concentration may include one of ionized calcium ($Ca^{2+}$) or a calcimimetic concentration determined via a calcimimetic model. In exemplary embodiments of the method, the model may be operative to use at least one stimulus function to facilitate the at least one PTG adaptation responsive to a deviation from the optimal range for one of the plurality of parameters.

In some embodiments of the method, the at least one stimulus function may be determined based on the following:

$$stim_W(x) = \frac{1}{1+\exp(-K_W(x-W_1))} + \frac{1}{1+\exp(-K_W(x+W_1))} - 1,$$

and W ∈ (C,D,P), wherein $K_w$ and $W_1$ are constants, wherein C refers to calcium concentration, D refers to vitamin D concentration, and P refers to phosphorous concentration.

In various embodiments of the method, CaSR expression and VDR expression may be determined based on the following:

$$\frac{dCaSR}{dt} = p_{Ca} \cdot (Ca^{in} + (VDR-1) - P^{in}) \cdot CaSR + n_{Ca} \cdot (1 - CaSR), \quad (1)$$

$$\frac{dVDR}{dt} = p_D \cdot (D^{in} + (CaSR-1) - P^{in}) \cdot VDR + n_D \cdot (1 - VDR), \quad (2)$$

$$\frac{dCa^{in}}{dt} = \\ (stim_C(CS-Ca_{opt}) \cdot (1-\text{sign}(stim_C(CS-Ca_{opt}))Ca^{in}) - Ca^{in}) \cdot \tau_C, \quad (3)$$

$$\frac{dD^{in}}{dt} = (stim_D(DS-D_{opt}) \cdot (1-\text{sign}(stim_D(DS-D_{opt}))D^{in}) - D^{in}) \cdot \tau_D, \quad (4)$$

$$\frac{dP^{in}}{dt} = (stim_P(P-P_{opt}) \cdot (1-\text{sign}(stim_P(P-P_{opt}))P^{in}) - P^{in}) \cdot \tau_P, \quad (5)$$

wherein $Ca_{opt}$ comprises an optimal blood value for calcium, $D_{opt}$ comprises an optimal blood value for vitamin D, $P_{opt}$ comprises an optimal blood value for phosphorous, P comprises a serum phosphate concentration, wherein $p_{Ca}$ and $p_D$ determine an intensity of a stimulus and feedback, a relationship between $p_{Ca}$ and $n_{Ca}$ and $p_D$ and $n_D$ determines the equilibrium of the system, wherein $Ca^{in}$, $D^{in}$, and $P^{in}$ are factors determining an effect of the stimulus on the CaSR expression and VDR expression, wherein $\tau_C$, $\tau_D$, and $\tau_P$ are time constants operative to determine a convergence rate to a steady state after a step-wise change in the calcium concentration, vitamin D concentration, or phosphate concentration.

In various embodiments of the method, the PTG functionality model may determine a sensed calcium concentration (CS) according to the following:

$$\frac{dCS}{dt} = sens(CaSR + VDR)C - CS, \quad (6)$$

$$\frac{dDS}{dt} = sens(CaSR + VDR)D - DS, \quad (7)$$

$$sens(x) = A_S + (1 - A_S) \cdot (x/2), \quad (8)$$

where C is the calcium concentration and D is the vitamin D concentration, wherein $A_s$ is a maximal rate of decay.

In exemplary embodiments of the method, the method may include determining at least one treatment recommendation based on the model output.

In accordance with various aspects of the described embodiments is a computer-implemented method of virtual PTG functionality analysis that may include, via a processor of a computing device, providing a calcimimetic model configured to simulate administration of a calcimimetic compound to a patient with at least one health abnormality affecting PTG function, the calcimimetic model may be operative to receive a calcimimetic dose, determine a concentration of the calcimimetic compound in at least one of a plurality of physiological compartments, each of the plurality of physiological compartments may be related to an adjacent physiological compartment via at least one constant rate function, and determine an output of a total calcimimetic concentration for at least one time period.

In some embodiments of the method, the calcimimetic compound may include cinacalcet. In various embodiments of the method, the plurality of physiological compartments may include an absorption compartment, a first pass metabolism compartment, a plasma free drug compartment, a plasma protein bound compartment, a fast tissue compartment, and a slow tissue compartment. In some embodiments of the method, the absorption compartment may be arranged adjacent to the first pass metabolism compartment and related via $k_a$ constant rate function. In various embodiments of the method, the calcimimetic model may be operative to determine a plurality of pharmacokinetic parameters simultaneously, the plurality of pharmacokinetic parameters comprising $C_{max}$, $t_{max}$, Bio, CL/F, $t_{1/2}$, $t_{1/2}^D$, and VD. In exemplary embodiments of the method, the output may be provided as a calcium concentration input of a PTG functionality model. In some embodiments of the method, the output may be provided as a calcium concentration input of a PTG functionality model via an operational model of allosterims configured to transfer the calcium concentration based on an amount of free drug in plasma.

In various embodiments of the method, the calcimimetic model may be operative to determine an amount of the calcimimetic compound in each compartment based on the following:

$$\frac{d\vec{y}}{dt} = A \cdot \vec{y}.$$

In some embodiments of the method, $\vec{y}_1$ may correspond to the amount of the calcimimetic compound in the absorption compartment, $\vec{y}_2$ may correspond to the amount of the calcimimetic compound in the first pass metabolism compartment, $\vec{y}_3$ may correspond to the amount of the calcimimetic compound in the plasma free drug compartment, $\vec{y}_4$ may correspond to the amount of the calcimimetic compound in the plasma protein bound compartment, $\vec{y}_5$ may correspond to the amount of the calcimimetic compound in the fast tissue compartment compartment.

In various embodiments of the method, the coefficient matrix A may be configured as follows:

$$A = \begin{pmatrix} -k_a & 0 & 0 & 0 & 0 \\ k_a & -k_e - k_{tp} & 0 & 0 & 0 \\ 0 & k_{tp} & -k_b - k_{PTF} - k_{PTs} - k_e^P & k_f & k_{TPf} \\ 0 & 0 & k_b & -k_f & 0 \\ 0 & 0 & k_{PTf} & 0 & -k_{TPf} \end{pmatrix}.$$

BRIEF DESCRIPTION OF THE DRAWINGS

By way of example, specific embodiments will now be described, with reference to the accompanying drawings, in which:

FIG. 5 depicts a table of an illustrative basic set of parameters for PTG, PTH release, and intracellular degradation in accordance with the present disclosure;

FIG. 6 depicts a table of an illustrative basic set of parameters for stimulus functions in accordance with the present disclosure;

FIG. 7 depicts a table of an illustrative basic set of parameters for time constants and intensity parameters for stimulus functions in accordance with the present disclosure;

FIG. 19 depicts a table of model parameters for a calcimimetic model in accordance with the present disclosure;

FIG. 20 depicts results generated via a simulation using a calcimimetic model in accordance with the present disclosure;

DETAILED DESCRIPTION

Figure 1:
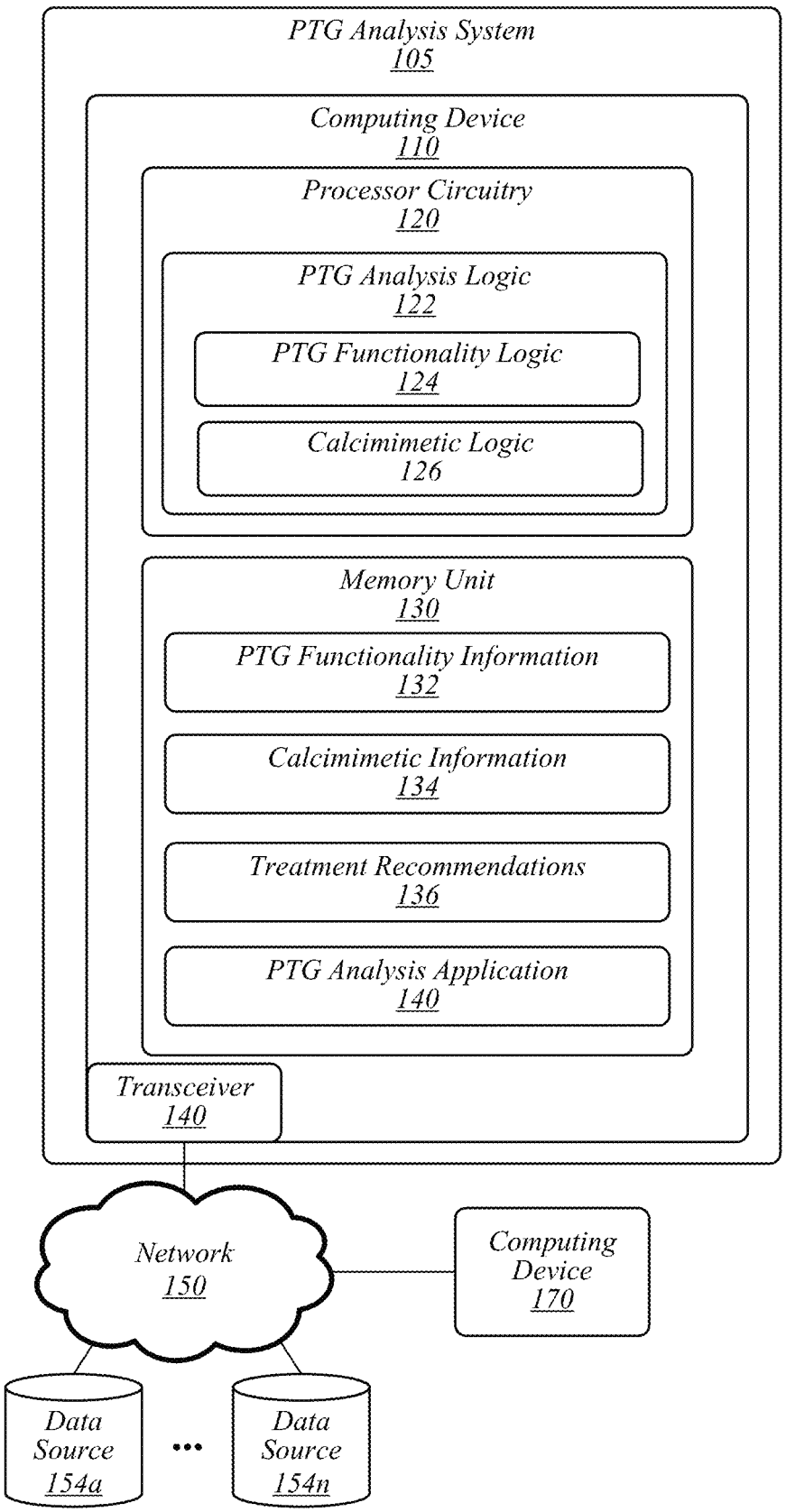
FIG. 1 illustrates a first exemplary operating environment in accordance with the present disclosure.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and convey the scope of the subject matter to those skilled in the art. In the drawings, like numbers refer to like elements throughout.

Altered parathyroid gland biology in patients with chronic kidney disease (CKD) is a major contributor to chronic kidney disease-mineral bone disorder (CKD-MBD). This disorder is associated with an increased risk of bone disorders, vascular calcification, and cardiovascular events. Parathyroid hormone (PTH) secretion is primarily regulated by the ionized calcium concentration (Ca or $Ca^{2+}$) as well as phosphate concentration (P) in the extracellular fluid and calcitriol, the bioactive form of vitamin D (D or 1,25D). Metabolic disturbances in patients with CKD may lead to alterations in the parathyroid gland (PTG) biology. A hallmark of CKD is secondary hyperparathyroidism, characterized by an increased production and release of PTH, reduced expression of calcium-sensing and vitamin D receptors on the surface of parathyroid cells, and hyperplasia and hypertrophy of these cells. These alterations happen on different time-scales and influence each other, thereby triggering a highly-complex cascade of negative and positive feedback loops. Due to this complexity, models may be used, inter alia, to break down the patterns of the multi-dimensional cascade of processes and enable the detailed study of subsystems.

In some embodiments, a PTG analysis process may use a PTG functionality model that includes the major adaptation mechanisms governing the production and secretion of PTH in patients with certain health abnormalities, such as CKD (for instance, and on hemodialysis (HD)). In addition, the PTG analysis process may include or use models for drugs targeting the parathyroid gland, such as a calcimimetic model operative to model the administration of calcimimetic compounds, for instance, a cinacalcet compound. Although the PTG analysis process, including the PTG functionality model and/or the calcimimetic model, may be used in examples with HD patients described herein with secondary hyperparathyroidism, embodiments are not so limited, as it is applicable to other clinical scenarios such as primary hyperparathyroidism, hypo- and hypercalcemia, and/or the like. In addition, although cinacalcet is used as an exemplary calcimimetic compound, embodiments are not so limited, as any calcimimetic compound capable of operating according to some embodiments is contemplated herein, for example, etecalcetide.

The concentration of extracellular ionized calcium is maintained within a narrow physiologic range by a biological system of negative and positive feedback regulators involving the major organs that transport calcium and phosphate, for instance, the intestine, kidneys, bones, endocrine glands, and, most prominently, the PTG. Under normal conditions, extracellular ionized calcium concentration ($Ca^{2+}$) is maintained within a narrow range of only about 1-2%.

A key endocrine regulator for serum $Ca^{2+}$ is PTH, which increases serum calcium levels by enhancing renal tubular calcium reabsorption, stimulating net bone resorption, and increasing the production of activated vitamin D (1,25-dihydroxyvitamin D3 or 1,25(OH)2D3) which increases net intestinal calcium absorption. PTH is produced, stored, and eventually released by the PTG. The PTG consists of two cell populations: active secretory cells and quiescent cells, which are able to proliferate or undergo apoptosis. Secretory active cells produce, store, and release PTH. PTG activity itself is mainly regulated by the calcium-sensing receptors (CaSR) on the surface of PTG cells.

The CaSR is integrally involved in PTG function and biology and, therefore, the key to understanding pathologies like secondary hyperparathyroidism. The activation of the CaSR by the binding of $Ca^{2+}$ initiates several signaling pathways which down-regulate PTH release, production, and PTG cellular proliferation rates. Moreover, the CaSR regulates PTH mRNA stability, thereby mediating its rate of degradation. Besides controlling PTH secretion, synthesis, degradation and PTG proliferation, the CaSR upregulates vitamin D receptor (VDR) expression.

The PTG adapts swiftly to conditions requiring enhanced PTH secretion, such as hypocalcemia. The different adaptive responses manifest on significantly different time scales, reaction times ranging from minutes to hours, to days, and weeks. For instance, in the case of an acute hypocalcemia, the PTG quickly responds by releasing stored PTH within seconds to minutes. If hypocalcemia persists, intracellular PTH degradation rate declines within 20 minutes, thereby increasing the amount of intact PTH that can be released. If normocalcemia is still not attained, the PTH production rate increases within an hour. Subsequently, the PTG will augment its cellular proliferation rate within two days. In chronic hypocalemia the enhanced proliferation rate will lead to hyperplasia whereby the PTG mass increases 10-100-fold or more.

In patients with chronic kidney disease (CKD) the loss of the regulatory kidney function triggers a cascade of processes eventually leading to secondary hyperparathyroidism, an abnormality characterized by increased PTH synthesis and secretion, and PTG cell proliferation. One hallmark of CKD is the impaired renal synthesis of the principal bioactive form of vitamin D, 1,25-dihydroxyvitamin D3 (1,25D), and the significantly impaired renal clearance of phosphate. Both 1,25D and phosphate significantly influence CaSR regulation, and thereby PTH synthesis and release, and PTG proliferation. There is a positive feedback loop between the CaSR and vitamin D receptor (VDR) expression, and a suppression of CaSR expression at high phosphate levels. The pathological effects exerted by high phosphate levels are significant. For example, studies in uremic rats have shown that a high phosphate diet enhances PTG proliferation within a few days. Low calcium intake has similar results but the required time is significantly longer. Importantly, the positive feedback loop of CaSR and VDR is effectively diminished in the presence of high phosphate levels.

In CKD, PTH stimulates bone resorption over bone formation, resulting in a net release of $Ca^{2+}$ and phosphate from the bone into the systemic circulation. As a consequence, PTH and phosphate levels increase even further and expression of CaSR and VDR is depressed, thus lowering the sensitivity of the PTG to Ca2+ and 1,25D. The altered biology eventually results in PTG hyperplasia and secondary hyperparathyroidism.

Due to the complexity of the adaptation of PTG biology in patients with CKD on hemodialysis, some embodiments may provide a PTG analysis process, which may include a PTG functionality model to analyze, evaluate, simulate, or otherwise examine the PTG under abnormal health conditions, such as secondary hyperparathyroidism, and to determine optimized treatment strategies. In tandem with mathematical models of bone turnover, intestinal calcium absorption, phosphate absorption, and/or the like, the PTG analysis process according to some embodiments may provide a key element of an in-silico model of PTG abnormalities, such as secondary hyperparathyroidism, for example, in CKD and HD patients. Accordingly, PTG analysis processes according to some embodiments may operate to generate predictions about the development of CKD-MBD and/or the treatment of CKD-MBD.

While there are various models of PTH activity in humans, conventional techniques fail to capture key adaptation mechanisms of the complex network regulating PTH and calcimimetic activity, particularly in patients with CKD or other health abnormalities that may affect PTG functions. In addition, due to the vast clinical use of calcimimetics, such as cinacalcet, a realistic model of CKD-MBD should feature the use of calcimimetics and their effects. Furthermore, to be of clinical use the calcimimetic model should be readily adaptable to various conditions, such as hepatic impairment enhancing cinacalcet exposure, and should be able to reflect different administration scenarios, including patient adherence to calcimimetic treatment regimens, which have been shown to be poor due to various issues.

Accordingly, some embodiments may provide a PTG analysis process that may include various models to simulate the functionality of the PTG and/or calcimimetic activity based on, for example, CaSR expression and activity regulated by ionized calcium (Ca or $Ca^{2+}$), phosphate (P), and vitamin D (D or 1,25D). Some embodiments may provide a multi-compartment calcimimetic model based on physiological considerations capturing all major pharmacokinetics parameters of a calcimimetic compound, such as cinacalcet.

Therefore, PTG analysis processes according to some embodiments may provide multiple technological advantages and technical features over conventional systems, including improvements to computing technology. One non-limiting example of a technological advantage may include modeling the various mechanisms ensuring enhanced PTH levels acting on different time scales, thereby allowing predictions for both rapid responses, for example, in the case of induced acute hypocalcemia, and long-term adaptations reflecting the transition of the healthy PTG into a hyperplastic gland with reduced sensitivity to $Ca^{2+}$ and 1,25D. Another non-limiting example of a technological advantage may include providing a calcimimetic model operative to provide intuitive individualization to various conditions or administration regiments and omit numerical instabilities in order to be easily implemented in other physiological models (for instance, a PTG functionality model according to some embodiments). A further non-limiting example of a technological advantage may include providing a PTG analysis process operative to generate treatment recommendations and/or determine research outcomes using virtual simulations of PTG functionality and/or calcimimetic administration without requiring clinical studies with actual patient participants. Other technological advantages are provided in this Detailed Description. Embodiments are not limited in this context.

FIG. 1 illustrates an example of an operating environment 100 that may be representative of some embodiments. As shown in FIG. 1, operating environment 100 may include a PTG analysis system 105. In various embodiments, PTG analysis system 105 may include a computing device 110 communicatively coupled to network 170 via a transceiver 160. In some embodiments, computing device 110 may be a server computer or other type of computing device.

Computing device 110 may be configured to manage, among other things, operational aspects of a PTG analysis process according to some embodiments. Although only one computing device 110 is depicted in FIG. 1, embodiments are not so limited. In various embodiments, the functions, operations, configurations, data storage functions, applications, logic, and/or the like described with respect to computing device 110 may be performed by and/or stored in one or more other computing devices (not shown), for example, coupled to computing device 110 via network 150 (for instance, one or more of client or peer devices 170). A single computing device 110 is depicted for illustrative purposes only to simplify the figure. Embodiments are not limited in this context.

Computing device 110 may include a processor circuitry that may include and/or may access various logics for performing processes according to some embodiments. For instance, processor circuitry 120 may include and/or may access a PTG analysis logic 122, PTG functionality logic 124, and/or calcimimetic logic 126. Processing circuitry 120, PTG analysis logic 122, PTG functionality logic 124, calcimimetic logic 126, and/or portions thereof may be implemented in hardware, software, or a combination thereof. As used in this application, the terms "logic," "component," "layer," "system," "circuitry," "decoder," "encoder," "control loop," and/or "module" are intended to refer to a computer-related entity, either hardware, a combination of hardware and software, software, or software in execution, examples of which are provided by the exemplary computing architecture 2100. For example, a logic, circuitry, or a module may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, a control loop, a computational model or application, an AI model or application, an ML model or application, a proportional-integral-derivative (PID) controller, variations thereof, combinations of any of the foregoing, and/or the like.

Although PTG analysis logic 122 is depicted in FIG. 1 as being within processor circuitry 120, embodiments are not so limited. For example, PTG analysis logic 122, PTG functionality logic 124, calcimimetic logic 126, and/or any component thereof may be located within an accelerator, a processor core, an interface, an individual processor die, implemented entirely as a software application (for instance, an PTG analysis application 140) and/or the like.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store various types of information and/or applications for an PTG analysis process according to some embodiments. For example, memory unit 130 may store PTG functionality information 132, calcimimetic information 134, treatment recommendations 136, and/or an PTG analysis application 140. In some embodiments, some or all of PTG functionality information 132, calcimimetic information 134, treatment recommendations 136, and/or an PTG analysis application 140 may be stored in one or more data stores 152a-n accessible to computing device 110 via network 150. For example, one or more of data stores 152a-n may be or may include a HIS, an EMR system, a dialysis information system (DIS), a picture archiving and communication system (PACS), a Centers for Medicare and Medicaid Services (CMS) database, U.S. Renal Data System (USRDS), a proprietary database, and/or the like.

Figure 2A:
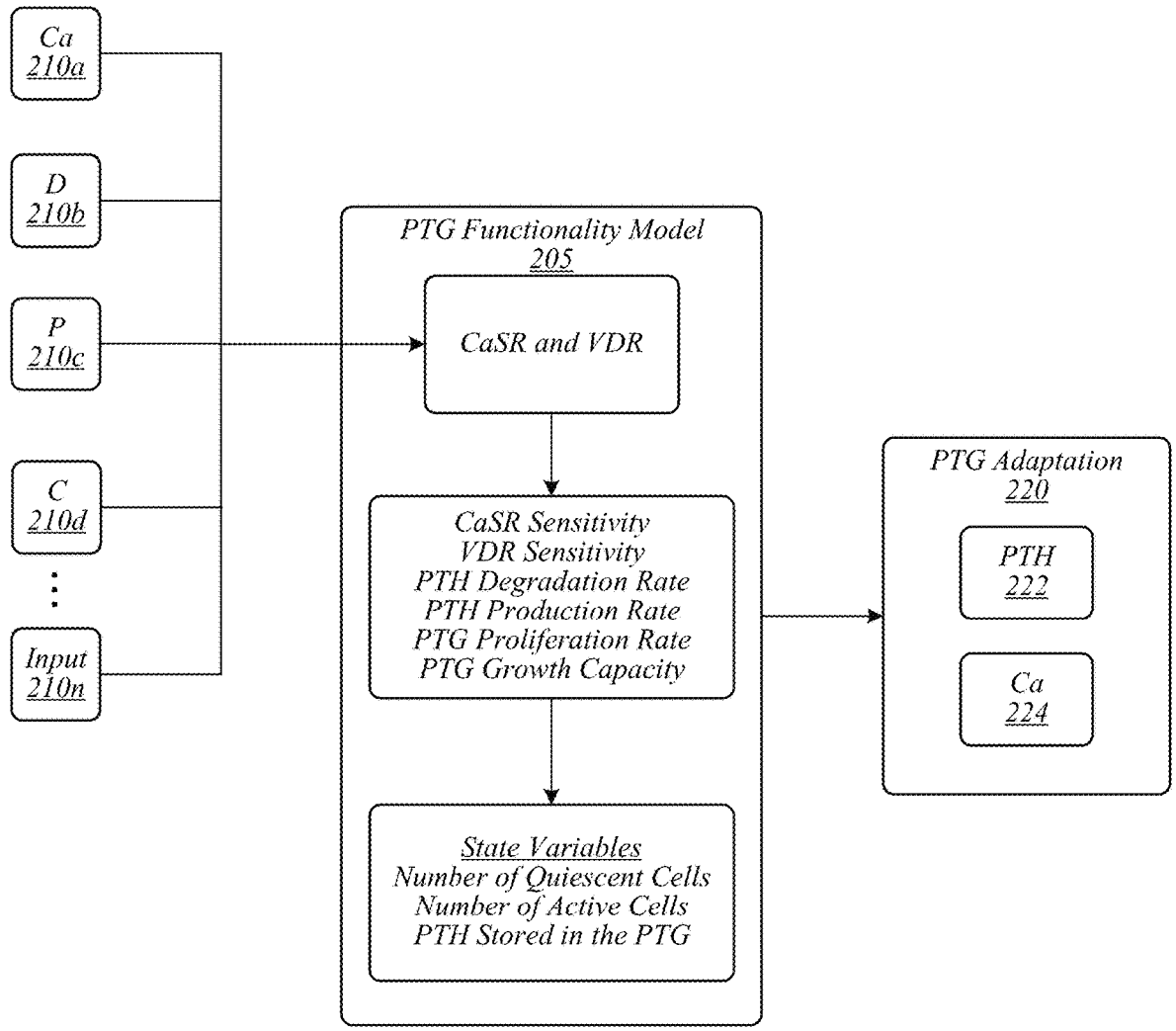
FIG. 2A illustrates a first block diagram of a parathyroid gland (PTG) functionality model in accordance with the present disclosure.
Figure 2B:
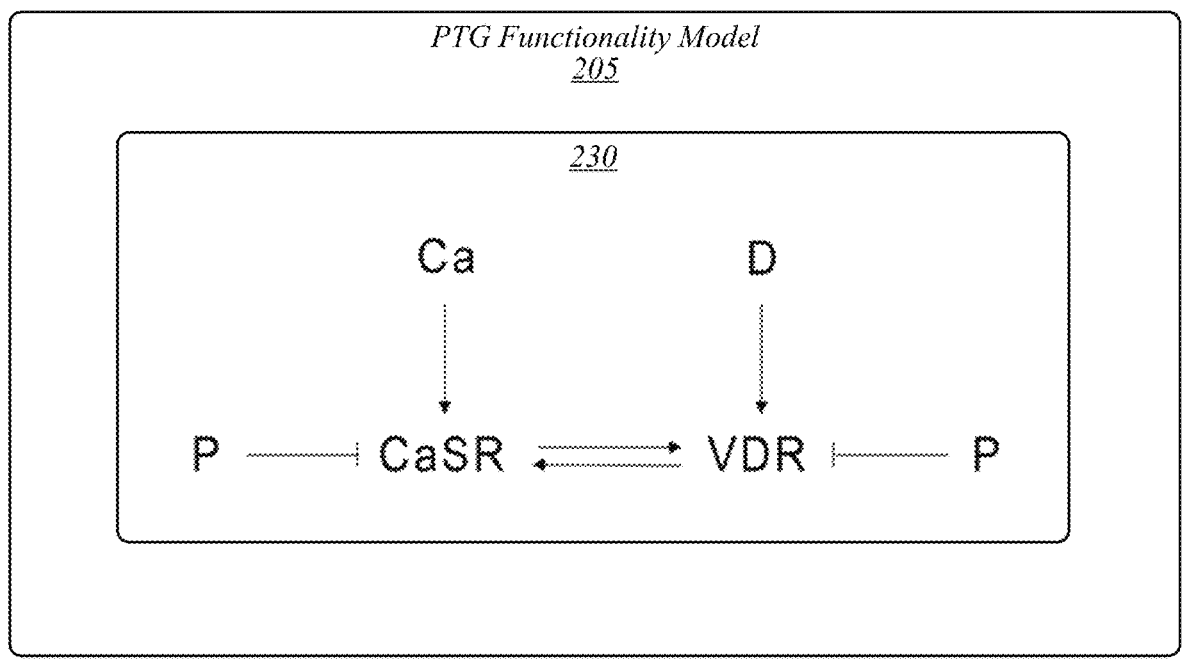
FIG. 2B illustrates a second block diagram of a PTG functionality model in accordance with the present disclosure.

In embodiments, PTG analysis logic 122, for example, via PTG functionality logic 124 and/or PTG analysis application 140, may operate to simulate PTG functionality via a PTG model. FIGS. 2A and 2B depict illustrative PTG functionality models according to some embodiments. Referring to FIG. 2A, therein is depicted PTG functionality model 205 operative to receive a plurality of inputs or parameters 210a-n associated with the functionality of various aspects of the PTG and to generate an output 220. In various embodiments, inputs 210a-n may include calcium concentration 210a, vitamin D (1,25D) concentration 210b, phosphorous concentration 210c, calcimimetic concentration 210d (for instance, via a calcimimetic model according to some embodiments). In some embodiments, $Ca^{2+}$, 1,25D, and P profiles used in PTH predictions in PTG functionality model 205 may be simulated profiles. In various embodiments, the in-silico data that is used as input 210a-n to PTG functionality model 205 may be within physiological meaningful ranges Ca2+. In exemplary embodiments, ionized calcium concentration 210a may be related to the PTG response via the CaSR. In some embodiments, $Ca^{2+}$, 1,25D, and P may be considered primary parameters.

Figure 10:
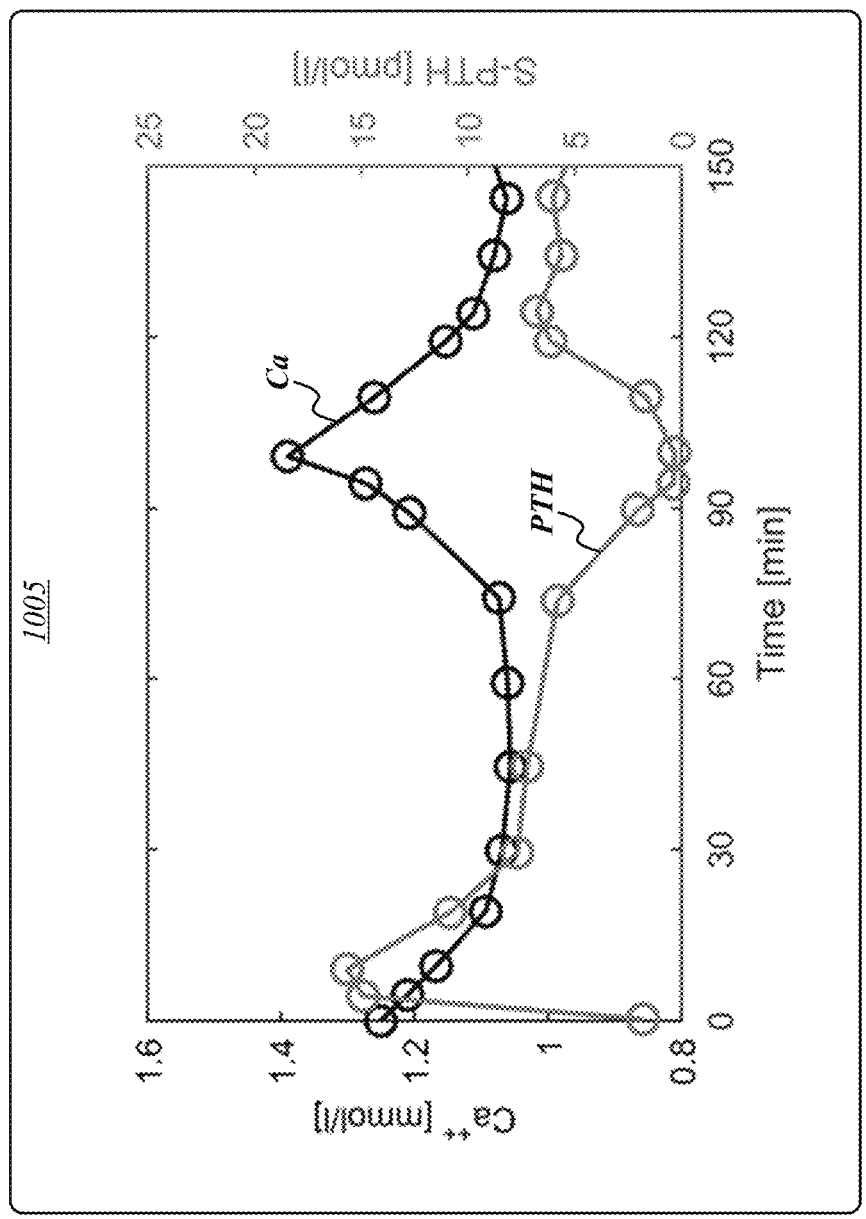
FIG. 10 depicts a graph of time versus $Ca^{2+}$ and predicted PTH concentrations in accordance with the present disclosure.

In exemplary embodiments, output 220 may be a PTG adaptation associated with the major adaptation mechanisms governing the production and secretion of PTH for patients with health abnormalities that affect PTH functionality, such as patients with CKD on HD. In various embodiments, the output 220 may be a PTH concentration 222 and/or calcium concentration 224, such as an ionized calcium (Ca or $Ca^{2+}$) concentration, a sensed calcium concentration (for instance, the concentration active on the CaSR), for example, at one or more particular time intervals (see, for example, FIGS. 10 and 11).

Referring to FIG. 2B, therein is depicted PTG functionality model 205 having a model structure 230. The core of PTG functionality model 205 is the CaSR. For model structure 230, while there is a positive feedback loop between the VDR and CaSR, CaSR and VDR expression may be suppressed by phosphate.

In some embodiments, PTG functionality model 205 does not model the structure of the CaSR; rather PTG functionality model 205 may operate using a few physiological principles governing the signaling cascade triggered by the CaSR: (1) if all key parameters (for instance, $Ca^{2+}$, 1,25D, and phosphate) are within their optimal range, the CaSR signaling will ensure that PTH release rate, production rate, and proliferation rate are down-regulated to their basal values and intracellular degradation rate is constant; (2) if one or more key parameters are not in their optimal range for a critical amount of time, CaSR signaling is altered resulting in PTG adaptations regarding PTH release rate, intracellular PTH degradation rate, PTH production rate, and cellular proliferation. The critical amount of time is significantly different for the different CaSR signaling pathways and is seconds for the release rate, minutes for the degradation rate, hours for the production rate, and days for the proliferation rate; (3) due to the feedback loops acting on the CaSR, the alteration in signaling also changes CaSR expression over time, for example, less CaSR expression leads to a lower sensitivity of the PTG to blood ionized calcium concentration; (4) PTG functionality model 205 may use stimulus functions describing the deviation from the optimal range, for example, negative stimulus may correspond to values below the optimal range, while positive stimulus may correspond to values above the optimal range; (5) stimulus functions may be the same for all adaptation mechanisms, for example, stimulus functions may be configured such that small deviations from the optimal value will not trigger a response unless these deviations last for an extended period of time; and (6) all effects but hyperplasia are reversible, for example, if a condition like acute hypocalcemia is resolved, PTH synthesis rate, intracellular degradation rate, and cellular proliferation rate may return to baseline; however, since apoptosis rate may be assumed to be constant, the PTG size may not decline. However, in certain instances, PTG size may decline if treated with certain drugs such as calcimimetics. They act on the apoptosis rate as well as the proliferation rate.

In reference to FIG. 1, PTG functionality information 132 may include information associated with PTG functionality logic 124, such as input information, parameters, models, model structures, outputs, thresholds, limits, constants, algorithms, equations, and/or the like. Embodiments are not limited in this context.

Figure 3A:
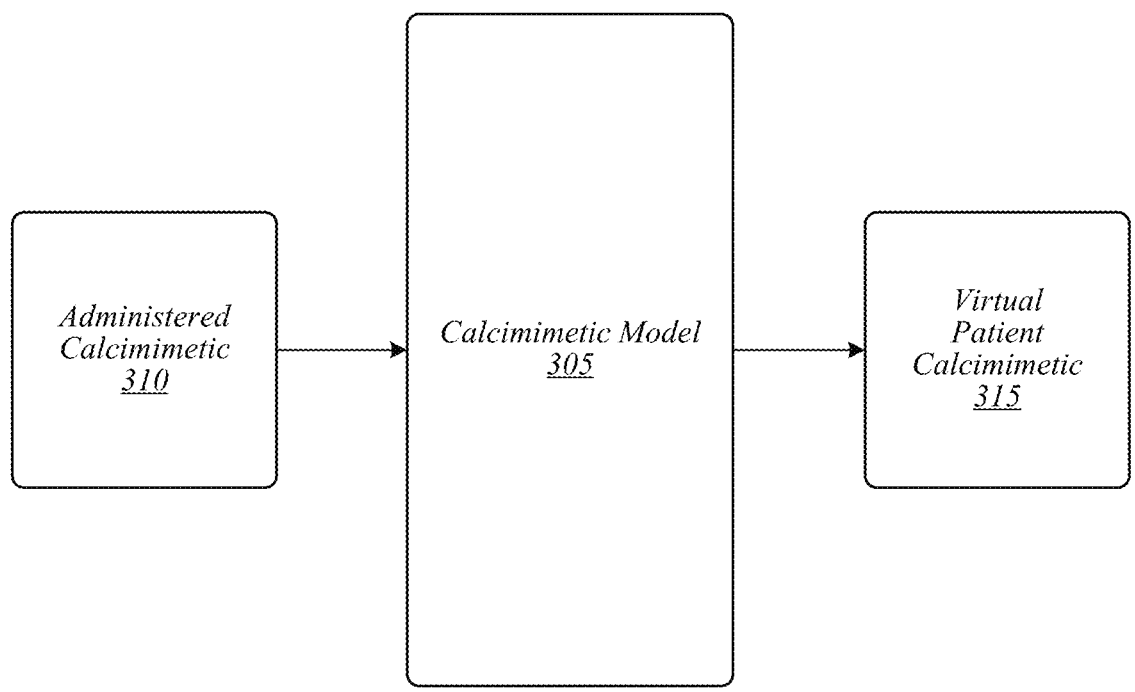
FIG. 3A illustrates a first block diagram of a calcimimetic model in accordance with the present disclosure.
Figure 3B:
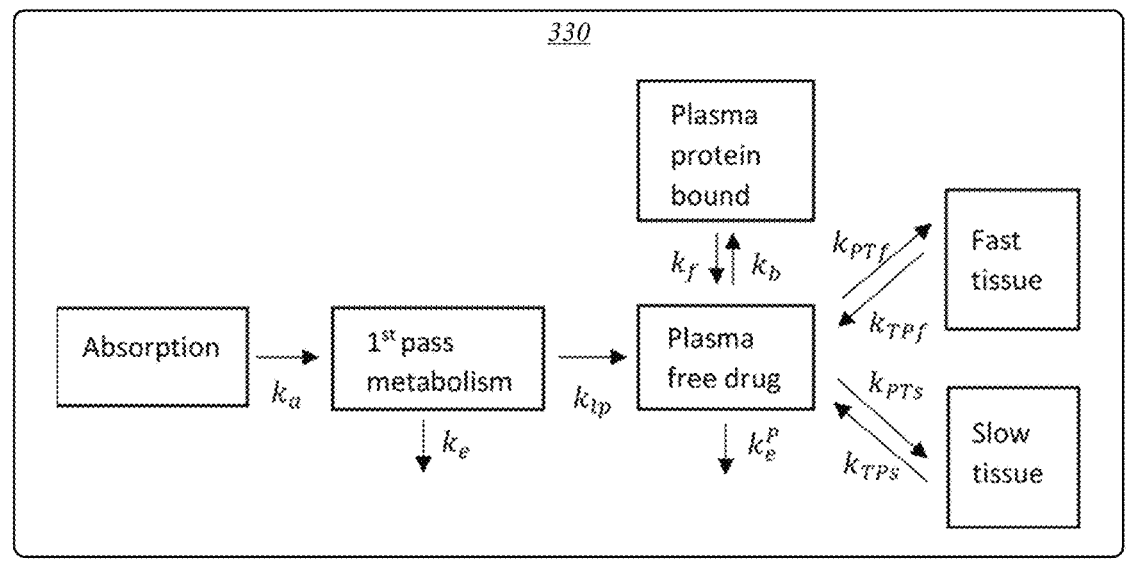
FIG. 3B illustrates a second block diagram of a calcimimetic model in accordance with the present disclosure.

In some embodiments, PTG analysis logic 122, for example, via calcimimetic logic 124 and/or PTG analysis application 140, may operate to simulate calcimimetic administration via a calcimimetic model. FIGS. 3A and 3B depict illustrative calcimimetic models according to some embodiments. Referring to FIG. 3A, therein is depicted calcimimetic model 305 configured to receive an administered calcimimetic concentration 310 as input and to generate a virtual patient calcimimetic concentration 315 as an output.

In some embodiments, calcimimetic model 305 may be a multi-compartmental model. Referring to FIG. 3B, therein is depicted calcimimetic model 305 with a multi-compartmental structure 330. For example, in some embodiments, calcimimetic model 305 may include six compartments including, without limitation, an absorption compartment, a first pass metabolism compartment, a plasma free drug compartment, a plasma protein bound compartment, a fast tissue compartment, and/or a slow tissue compartment. Although calcimimetic model 305 may be described with six compartments, embodiments are not so limited as calcimimetic model 305 may include more or less compartments. For example, in some embodiments, calcimimetic model 305 may not include a slow tissue compartment.

Calcimimetic information 134 may include information associated with calcimimetic logic 126, such as input information, parameters, models, model structures, outputs, thresholds, limits, constants, algorithms, equations, and/or the like. For example, to assess the impact of dosing regiments on the total exposure calcimimetic model 305 may use the weekly average calcimimetic (for instance, cinacalcet) concentration in the blood for three different dosing regiments: daily administration, administration three times a week, and administration with a realistic patient refill rate of 64%. Embodiments are not limited in this context.

In reference to FIG. 1, PTG analysis logic 122 may operate to determine predictions relating to PTG functionality (for instance, PTH concentrations for various $Ca^{2+}$, 1,25D, and/or P inputs) and calcimimetic activity (for instance, cinacalcet concentrations at certain time intervals for a particular dosage scheme). In some embodiments, PTG analysis logic 122, alone or in combination with PTG analysis application, may generate one or more treatment recommendations 136 based, at least in part, on information generated by PTG functionality models and/or calcimimetic models according to exemplary embodiments. For example, a PTG functionality model may be developed for certain patient populations, such as age, weight, disease state, health abnormality, and/or the like. In another example, a calcimimetic model may be generated for certain patient populations and/or dosing regimens. PTG analysis logic 122 may determine a treatment recommendation for a patient that fits within a modeled patient population to generate a potential treatment recommendation 136. In some embodiments, treatment recommendations 136 may include diagnoses of abnormal health conditions, potential causes of abnormal health conditions, and/or the like.

In some embodiments, for a PTG functionality model (such as model 205), CaSR and VDR expression are determined in order to assess the overall sensitivity of the receptors to the concentration of blood ionized calcium and 1,25D concentrations. A PTG functionality model may include or may use a dimensionless CaSR and VDR expression. The optimal value may be normalized to 1 for both variables. Values lower than 1 may correspond to a loss of CaSR or VDR expression. Receptor expression may be regulated by a positive feedback loop between the CaSR and the VDR (FIG. 2B) and is suppressed by phosphate. Conventional approaches typically involve delay equations. However, these equations are numerically highly unstable and challenging (or even impossible) to simulate even a couple of months with delay equations. Accordingly, some embodiments operate to simulate the alterations of PTG biology using feedback loops or equations as described herein, which may operate to make fast, accurate, and realistic modeling of PTG biology possible.

In some embodiments, the dimensionless CaSR expression, CaSR, and VDR expression, VDR, are governed by the following system of differential equations (1)-(8):

$$\frac{dCaSR}{dt} = p_{Ca} \cdot (Ca^{in} + (VDR - 1) - P^{in}) \cdot CaSR + n_{Ca} \cdot (1 - CaSR), \quad (1)$$

$$\frac{dVDR}{dt} = p_D \cdot (D^{in} + (CaSR - 1) - P^{in}) \cdot VDR + n_D \cdot (1 - VDR), \quad (2)$$

$$\frac{dCa^{in}}{dt} = \quad (3)$$
$$(stim_C(CS - Ca_{opt}) \cdot (1 - \text{sign}(stim_C(CS - Ca_{opt}))Ca^{in}) - Ca^{in}) \cdot \tau_C,$$

$$\frac{dD^{in}}{dt} = (stim_D(DS - D_{opt}) \cdot (1 - \text{sign}(stim_D(DS - D_{opt}))D^{in}) - D^{in}) \cdot \tau_D, \quad (4)$$

$$\frac{dP^{in}}{dt} = (stim_P(P - P_{opt}) \cdot (1 - \text{sign}(stim_P(P - P_{opt}))P^{in}) - P^{in}) \cdot \tau_P, \quad (5)$$

where $Ca_{opt}$, $D_{opt}$, and $P_{opt}$ are the optimal blood values of $Ca^{2+}$, 1,25D, and phosphate. CS and DS are defined in equations (6) and (8), below, and couple the actual blood values of $Ca^{2+}$ and 1,25D with the receptor density. P is the serum phosphate concentration. The intensity of the stimulus and feedback may be governed by $p_{Ca}$ and $p_D$, the relationship between $p_{Ca}$ and $n_{Ca}$ as well as $p_D$ and $n_D$ determines the equilibrium of the system. $Ca^{in}$, $D^{in}$, and $P^{in}$ are factors determining the effect of the stimulus of Ca, D, and P, respectively, on the CaSR and VDR. The time constants $\tau_C$, $\tau_D$, and $\tau_P$ determine the convergence rate to the steady state after a step-wise change in calcium, 1,25D, and/or phosphate. They are associated with the critical time after which the system starts to react to non-optimal concentrations of ionized calcium, 1,25D, or phosphate. The stimulus functions may be written according to the following equation (StFx):

$$stim_W(x) = \frac{1}{1 + \exp(-K_W(x - W_1))} + \frac{1}{1 + \exp(-K_W(x + W_1))} - 1,$$

and W∈ (C,D,P), (StFx)
where K and $W_1$ are constants. Under optimal conditions, the stimulus functions may be zero for calcium, 1,25D, and phosphate. Therefore, $Ca^{in}$, $D^{in}$, and $P^{in}$ are zero and the CaSR and VDR expression is not altered. If the deviation from the optimal range is shorter than the critical time associated with the time constants, for example, a brief induced hypocalcemia, the stimulus on $Ca^{in}$ is too small to change $Ca^{in}$ significantly. Therefore, CaSR expression will not be altered. However, in the case of a mild but chronic hypocalcemia, CaSR expression will slowly decline after a time lag due to the small but constant stimulus of $Ca^{in}$.

A lower density of CaSR may lead to less downstream signalling. Therefore, the same actual $Ca^{2+}$ concentration can lead to different PTG responses in a healthy PTG compared to a gland with reduced CaSR expression. The gland with reduced CaSR expression appears less sensitive to $Ca^{2+}$. Therefore, it is not the present ionized calcium level that determines the response of the system but rather the calcium and level associated with the CaSR density which is referred to as sensed calcium concentration CS:

$$\frac{dCS}{dt} = sens(CaSR + VDR)C - CS, \qquad (6)$$

$$\frac{dDS}{dt} = sens(CaSR + VDR)D - DS, \qquad (7)$$

$$sens(x) = A_S + (1 - A_S) \cdot (x/2), \qquad (8)$$

where C is the blood ionized calcium concentration and D is the 1,25D plasma concentration. At optimal conditions, the dimensionless CaSR and VDR expressions may equal 1, and CS and DS equilibrates to c and D. Hence, the sensed calcium concentration may equal the actual blood $Ca^{2+}$ concentration. If the dimensionless CaSR expression starts to decline, the sensed calcium concentration CS declines as well, but with a slight delay. The maximal rate of decline is $A_s$. This effect may be reversible. If the CaSR expression increases again, for instance, by long-term effects of a low phosphate diet, 1,25D supplements, or calcimimetics, the sensed calcium concentration CS will approach C again.

CaSR signaling is directly governed by the sensed ionized calcium concentration CS and phosphate. Further, the activity is indirectly governed by VDR due to the feedback loop between the VDR and CaSR:

$$\frac{dC_o}{dt} = p_o \cdot (Ca^{in} - P^{in}) \cdot C_o + n_o \cdot (1 - C_o), \qquad (9)$$

$$\frac{dCa_o^{in}}{dt} = \left(stim_{Ca}(CS - Ca_{opt}) \cdot \left(1 - \frac{stim_{Ca}}{|stim_{Ca}|}Ca^{in}\right) - Ca^{in}\right) \cdot \tau_{Ca}^o, \qquad (10)$$

$$\frac{dP_o^{in}}{dt} = \left(stim_P(P - P_{opt}) \cdot \left(1 - \frac{stim_P}{|stim_P|}P^{in}\right) - P^{in}\right) \cdot \tau_P^o. \qquad (11)$$

Again, $p_o$ and $n_o$ determine the intensity of the stimulus on the activity, whereas the time constants $\tau_{Ca}^o$ and $\tau_P^o$ determine the critical time with which the system responses to the stimulus. These sets of equations may be used for the cellular degradation rate (o=d), PTH production rate (o=p), and cell proliferation rate (o=pr).

Under normal conditions (i.e. $C_d \geq 1$), CaSR keeps the cellular degradation of PTH $k_d$ at a basal rate of $A_d$. If not regulated by the CaSR, this rate will decrease to a minimum rate of $B_d = 0.5 \cdot A_d$:

$$k_d = B_d + (A_d - B_d) \cdot C_d \text{ for } C_d < 1 \qquad (12)$$

PTH is constantly produced by secretory active PTG cells with a basal rate of $A_p$. Again, if not down-regulated by the CaSR, the production rate k will increase within minutes to hours to a maximum level of $B_p = 2 \cdot A_p$:

$$k_p = B_p + (A_p - B_p)C_p \text{ for } C_p < 1. \qquad (13)$$

The cell proliferation rate $k_{pr}$ increases from the basal level $A_{pr}$ to a maximum rate of $B_{pr} = 2 \cdot A_{pr}$ if not down-regulated by the CaSR [References 114 and 118]:

$$k_{pr} = B_{pr} + (A_{pr} - B_{pr}) \cdot C_{pr} \text{ for } C_{pr} < 1 \qquad (14)$$

A PTG functionality model according to some embodiments may employ two cell populations, active secretory cells S and quiescent cells Q. PTG cells cycle through the two states. For example, cells in the quiescent state can proliferate or undergo apoptosis and, when left untreated, enhanced cell proliferation will lead to PTG hyperplasia. This behavior may be simulated in a PTG functionality model by a tumor model with dynamic carrying capacity K. Associating the total number of cells in the quiescent state with the volume with PTG functionality model may be determined according to the following:

$$\frac{dS}{dt} = -k_{SQ}S + k_{QS}Q, \qquad (15)$$

$$\frac{dQ}{dt} = k_{SQ}S - k_{QS}Q - k_aQ + k_{pr}Q\ln(K/(S+Q)), \qquad (16)$$

$$\frac{dK}{dt} = k_k((S+Q)/(S_0+Q_0) - 1)^{2/3}, \qquad (17)$$

where $k_{SQ}$ and $k_{QS}$ are constant rates determining the cell cycle between the secretory active and quiescent state, $k_a$ is the constant apoptosis rate, and the constant $k_k$ is the rate with which the dynamic growth capacity K adjusts to the size of the gland. The size of the healthy gland may be estimated by the initial steady state $S_0 = S(0)$, $Q_0 = Q(0)$.

Figure 4:
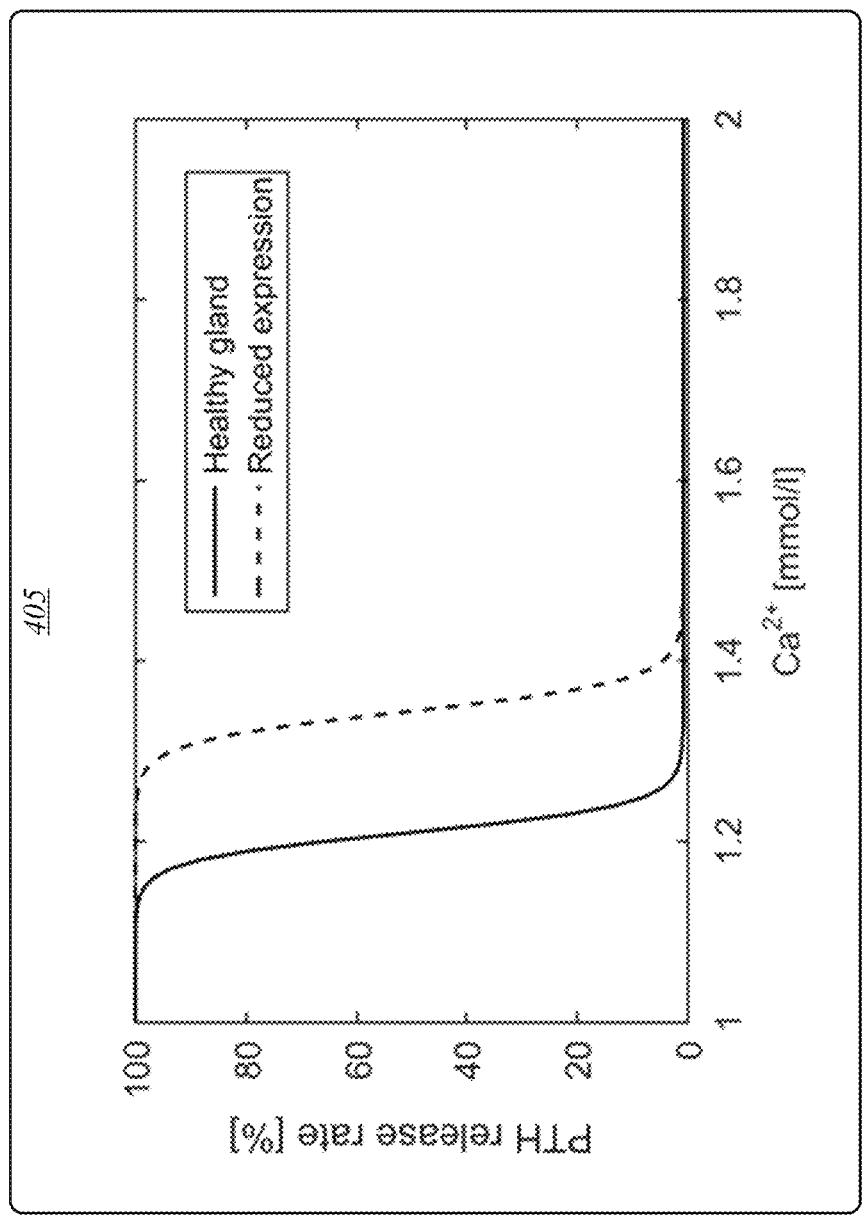
FIG. 4 depicts a graph of parathyroid hormone (PTH) release rate as a function of ionized calcium ($Ca^{2+}$) in accordance with the present disclosure.

There is a sigmoidal relationship between $Ca^{2+}$ and PTH release rate. The following sub-model may be used to model storage of PTH in the gland:

$$\frac{dPTG}{dt} = k_pS - release(CS)PTG - k_dPTG, \qquad (18)$$

$$\frac{dPTH}{dt} = release(CS)PTG - k_{cl}PTH, \qquad (19)$$

$$release(CS) = B + (A - B)\frac{1}{1 + (CS/S_r)^n}, \qquad (20)$$

where PTG and PTH are the PTH concentrations in the gland and serum, respectively. In healthy subjects, with phosphate and 1,25D levels in the normal range, PTG will react quickly to changes in ionized calcium concentrations by either releasing a high amount of PTH in the case of a drop in Ca2+ or by suppressing the release of PTH in the case of excess Ca2+ concentrations. However, if CaSR sensitivity is reduced, i.e. in the case of chronic hyperphosphatemia or reduced 1,25D plasma levels, the release function is automatically shifted, mimicking a shift in the setpoint S, (see, for example, graph 405 of FIG. 4). The PTG cannot react properly to normal $Ca^{2+}$ levels or even to slightly higher $Ca^{2+}$ concentrations. FIG. 4 depicts graph 405 of PTH release rate as a function of $Ca^{2+}$. A reduced expression of CaSR results in a shift of the release function.

In the example, of FIG. 4, CS equals 90% of the actual ionized calcium concentration.

In various embodiments, the only parameters estimated for the simulations are parameters associated with the intensities of the feedback systems (Equations (1), (2), (6), and (9)). All basic parameters for PTG, PTH release, and intracellular degradation are based various customary values (see, for example, table 505 of FIG. 5). Basic parameters for the stimulus functions (see, for example, table 605 of FIG. 6) may be chosen such that the derivative of the stimulus function is maximal around the critical values ($Ca^{2+}$ (arterial blood ionized calcium): 2.8 mg/dl, 1,25D: 90 ng/ml, P: 6.6 mg/dl) and the mean derivative in the reference range (Ca2+: 4.4-5.5 mg/dl, 1,25D: 20-60 ng/dl, P: 3.4-4.5 mg/dl) is smaller than 0.08 for $Ca^{2+}$ and P, and 0.0035 for 1,25D. The value for 1,25D is much smaller since it is not as tightly regulated as the other two parameters. FIG. 5 depicts table 505 of an illustrative basic set of parameters for PTG, PTH release, and intracellular degradation according to some embodiments. In some embodiments, $k_{QS}$ may be selected such that the fraction of active cells may be at a steady state of 0.2. FIG. 6 depicts table 605 of an illustrative basic set of parameters for stimulus functions according to some embodiments.

In some embodiments, time constants may be chosen such that the effect of the stimulus is physiologically reasonable (see, for example, table 705 of FIG. 7). FIG. 7 depicts table 705 of an illustrative basic set of parameters for time constants and intensity parameters for stimulus functions according to some embodiments. In various embodiments, alterations with the exception of cellular proliferation reach a steady state. Therefore, in some embodiments, the only time constant relevant for long-term adaptations is the one associated with cellular proliferation. In some embodiments, the impact of uncertainties in the time constant may be evaluated by multiplying or dividing the base time constants (equations (10) and (11)) governing the response of the cellular proliferation rate to the stimulus (equation (14)) one at a time by a factor of 10 while keeping all other parameters constant and simulating a mild hypocalcemia and hyperphosphatemia. In some embodiments, PTG functionality models according to some embodiments are not sensitive to the alterations of the time constants. For example, even after 30 days the difference in PTH is below 0.009% for changes in phosphate related values and below 0.003% for changes in calcium-related values.

The sensitivities of PTH predictions related to uncertainties of intensities of the stimulation functions may be assessed by multiplying or dividing the base values by a factor 2 one at a time while keeping all other parameters constant. For example, PTH may be simulated for 7 days under the condition of normocalcemia, developing hyperphosphatemia, and declining 1,25D levels. Such an analysis may reveal that the highest sensitivity to changes of $p_{Ca}$ and $n_{Ca}$ associated with PTH production rate (equations (9), (13)) and to changes of $p_{Ca}$ and $n_{Ca}$ of the CaSR (equations (1)-(2)) determining the steady state of the CaSR expression.

Figure 8:
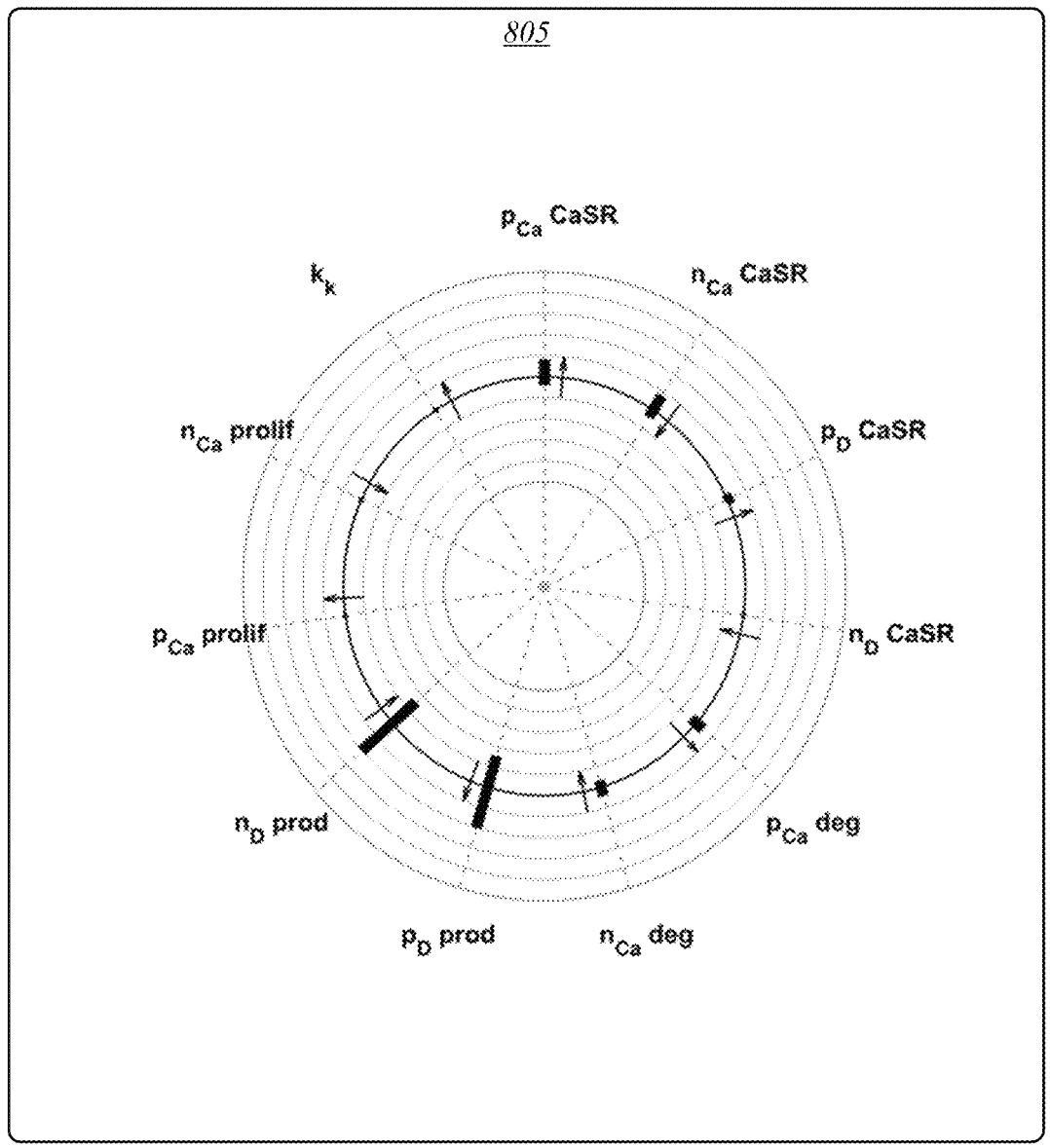
FIG. 8 depicts a sensitivity plot of PTH predictions to changes in various parameters in accordance with the present disclosure.

FIG. 8 depicts a sensitivity plot or graph 805 according to some embodiments. For example, sensitivity plot 805 may be a plot of PTH predictions to changes in various parameters. Plot 805 may depict the maximum deviation from reference PTH values as the ratio between the calculated PTH and the reference PTH. For example, the smallest circle may correspond to a relative deviation of 0.5, the largest circle to a relative deviation of 1.5. Arrows pointing outwards indicate that higher parameter values lead to higher PTH values; arrows pointing outwards indicate that higher parameter values lead to smaller PTH values.

The acute response of PTH to hypocalcemia depends on the rate of $Ca^{2+}$ reduction. For example, a massive linear drop by 1.6 mg/dl $Ca^{2+}$ within 30 minutes produced a prominent PTH peak. A linear drop of the same amount within 120 minutes may not produce a prominent PTH peak but higher PTH concentrations after around 60 minutes.

Case Study I: PTG Functionality Model Simulation

Figure 9:
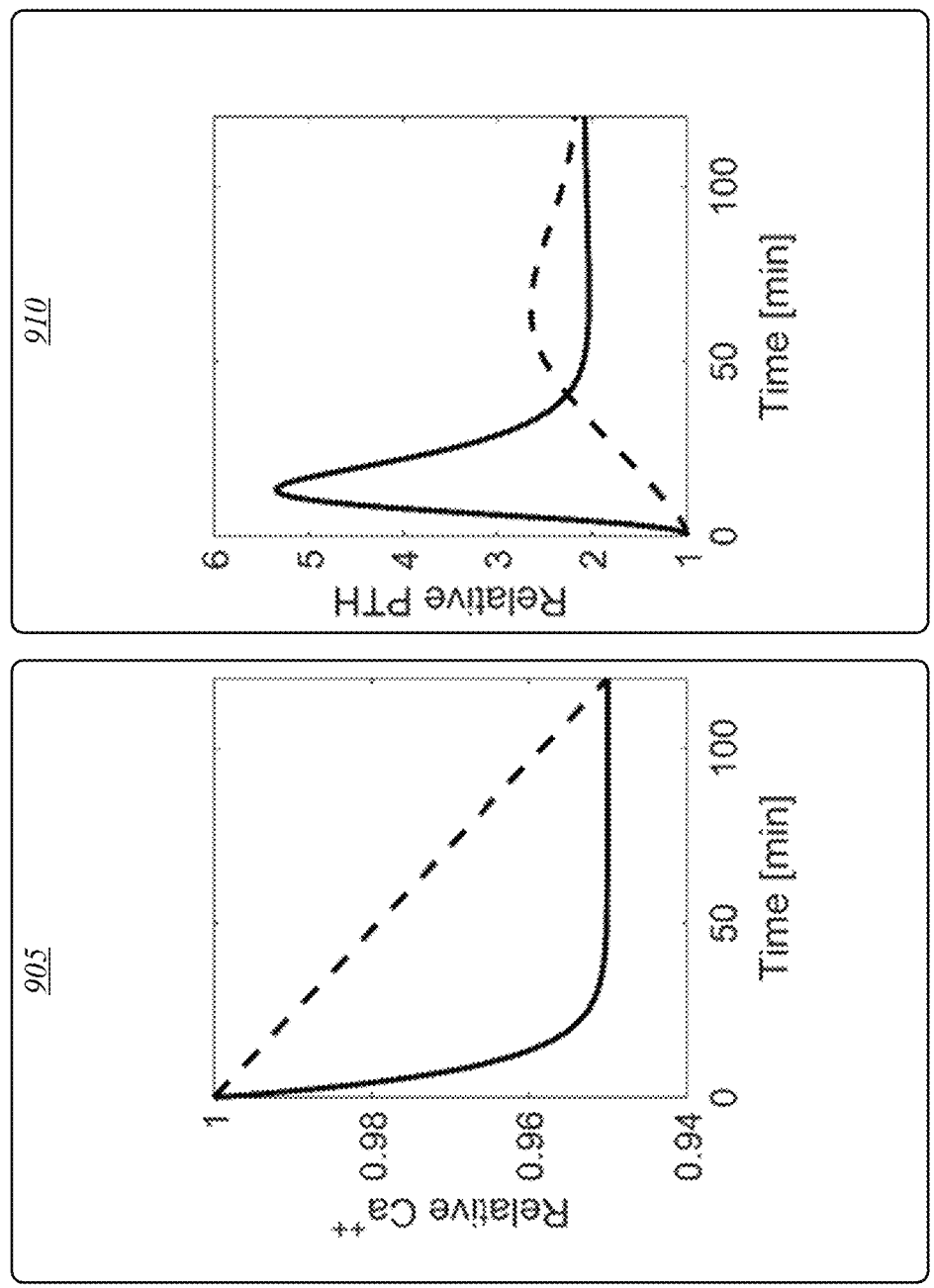
FIG. 9 depicts graphs of time versus $Ca^{2+}$ and predicted PTH concentrations in accordance with the present disclosure.

A simulation was performed using a PTG functionality model according to some embodiments simulating an acute $Ca^{2+}$ change by starting from the system steady state and changing the ionized calcium concentration at different rates. Due to the storage of PTH in the secretory active cells, fast induction of hypocalcemia (5% reduction of Ca2+ within 30 minutes) leads to the clinically observed PTH overshoot followed by a sharp decline, while slow induction of hypocalcemia (5% reduction of Ca2+ within 120 minutes) leads to a small PTH overshoot before reaching levels similar to those of the fast reduction protocol (see, for example, graphs 905 and 910 of FIG. 9). FIG. 9 depicts graphs 905 and 910 of time versus $Ca^{2+}$ and predicted PTH concentrations during induced hypocalcemia, respectively, according to some embodiments. While PTH response shows a prominent peak when the rate of calcium reduction is high (solid line), the peak is almost diminished when the rate of change is low (dashed line).

In some embodiments, induced hypocalcemia followed by a brief return to normocalcemia and a subsequent hypocalcemia may be used to analyze PTH hysteresis effects. After a sharp increase of PTH during the first peak of 0.8 mg/dl from $Ca^{2+}$ baseline levels and a slight drop due to the return to normal, PTG functionality model did not observe a second transient PTH peak (see, for example, graph 1005 of FIG. 10 during induced hypocalcemia, normocalcemia and subsequent hypocalcemia).

Figure 11:
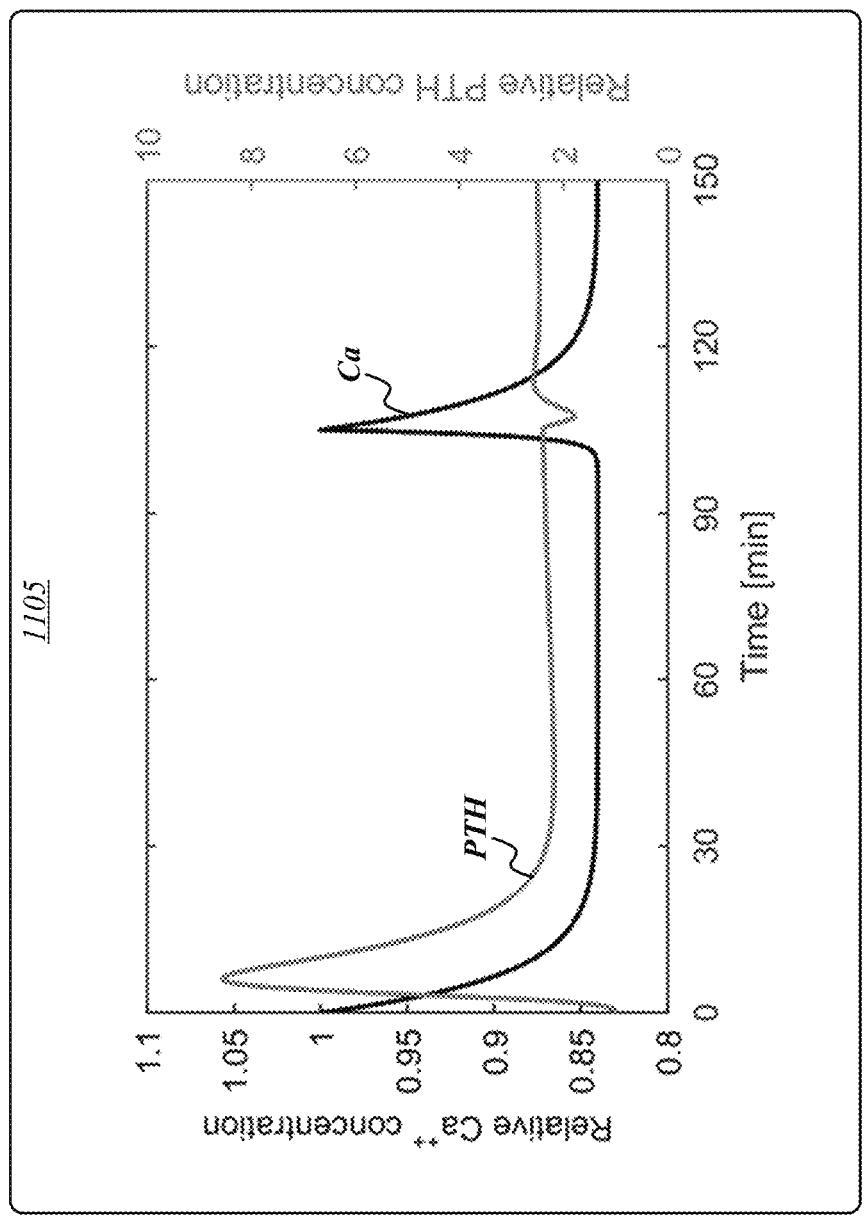
FIG. 11 depicts a graph of time versus relative $Ca^{2+}$ and relative PTH concentrations in accordance with the present disclosure.

Results of Case Study I indicated a prominent peak during the first hypocalcemia (due to the quick release of PTH stored in the PTG cells) and no peak during the second hypocalcemia (since recovery time in the normocalcemic condition is insufficient to load the PTH storage again) (see, for example, graph 1105 of FIG. 11 during induced hypocalcemia, normocalcemia and subsequent hypocalcemia).

Figure 12:
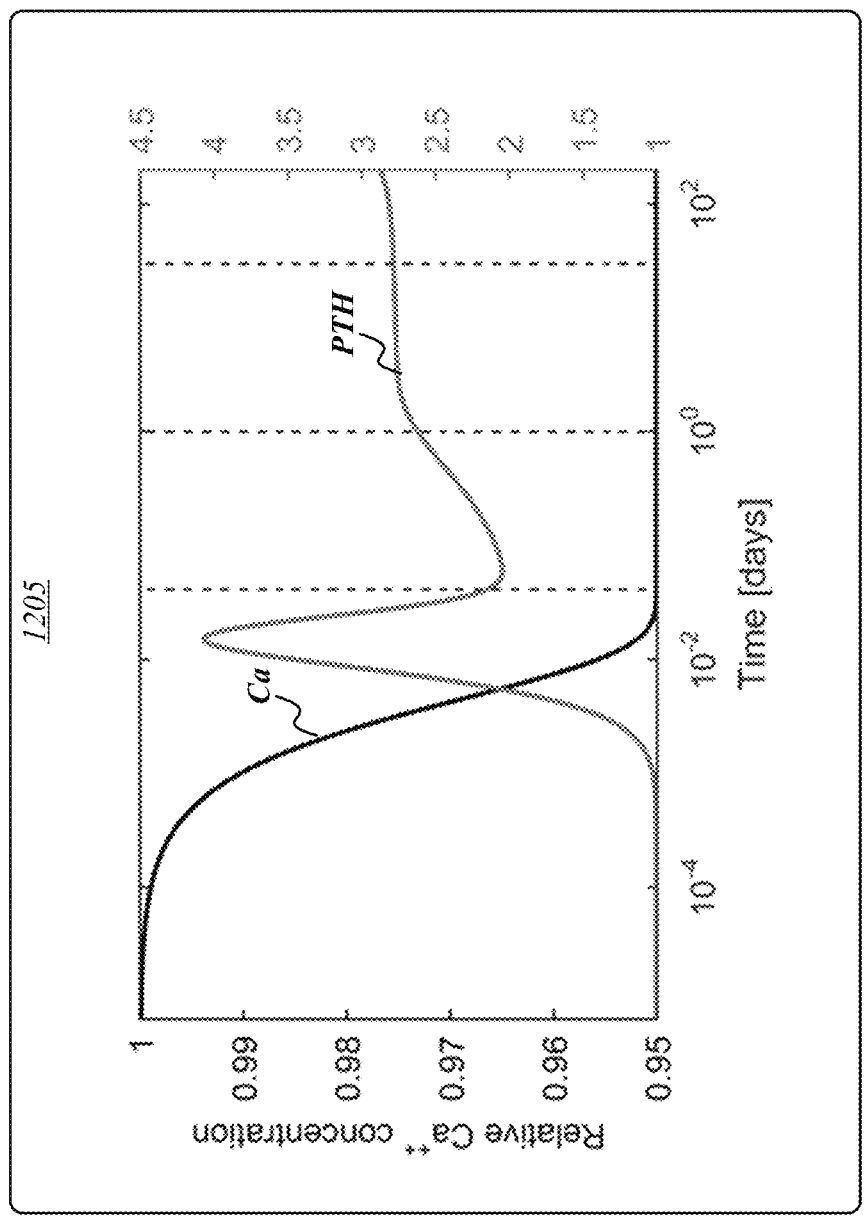
FIG. 12 depicts a graph of time versus $Ca^{2+}$ and predicted PTH concentrations in accordance with the present disclosure.

Mild but chronic hypocalcemia may trigger all mechanisms resulting in elevated PTH levels. In Case Study I, chronic hypocalcemia was simulated by lowering Ca2+ by 0.25 mg/dl and keeping it low for 200 days. Due to the slight decline in CaSR expression, the decrease in intracellular degradation, the increase in PTH production rate and the slight increase in cellular proliferation, PTH levels will not reach a steady state but rather increase slightly but steadily (see, for example, graph 1205 of FIG. 12). FIG. 12 depicts graph 1205 of Time versus $Ca^{2+}$ and PTH concentrations during induced chronic hypocalcemia. The time scale is logarithmic, the black vertical dashed lines indicate one hour, one day, and one month.

Figure 13:
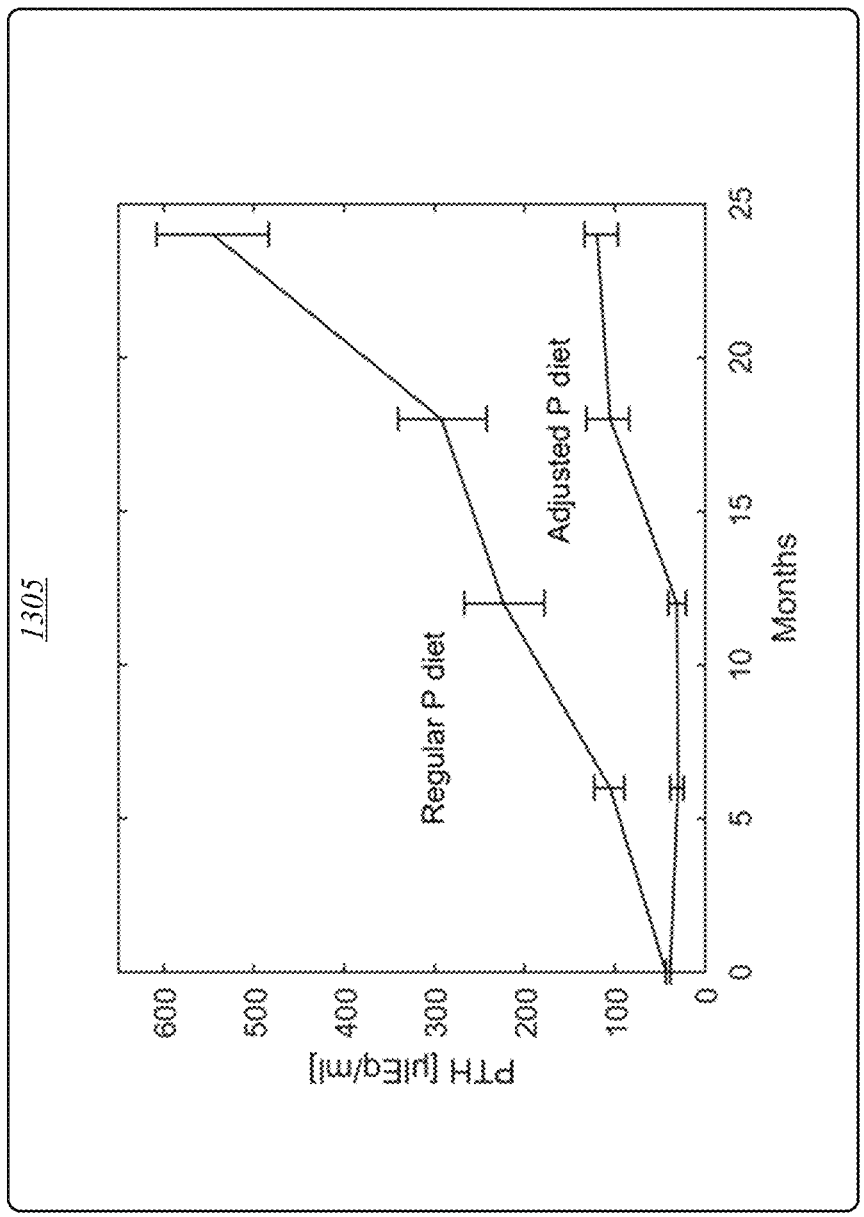
FIG. 13 depicts a graph of time versus PTH concentrations in accordance with the present disclosure
Figure 14:
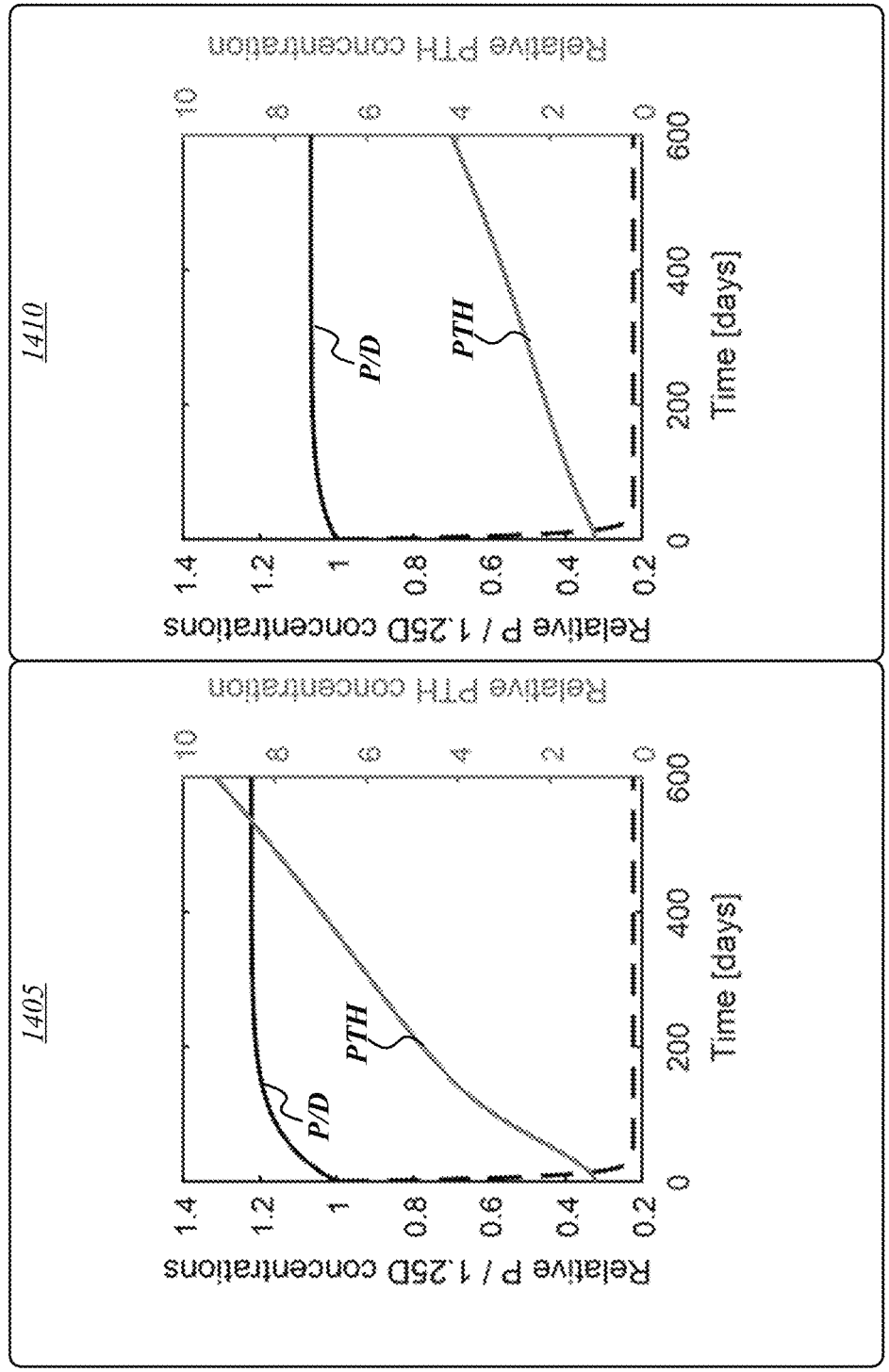
FIG. 14 depicts graphs of time versus relative phosphorous (P) and vitamin D (1,25D) and relative PTH concentrations in accordance with the present disclosure.

A steady increase of PTH can also be observed if $Ca^{2+}$ is kept at an optimal value, but 1,25D is reduced (for example, due to impaired synthesis), and phosphate levels are elevated (for example, due to impaired clearance, see FIG. 9). Although there is no prominent PTH peak because $Ca^{2+}$ is maintained at the optimal level, the PTH concentration will continuously increase and not reach a steady state due to the loss of CaSR expression and sensitivity and the increased cellular proliferation. Previous studies indicated long-term effects of phosphate diets and calcitriol supplementation on PTH levels, with PTH levels due to regular phosphate intake rising steadily over a long duration (for instance, over two years), with an endpoint of almost ten-fold above the normal levels. An increase in the slope was significantly lower if phosphate intake was lowered in line with the decreased glomerular filtration rate (see, for example, graph 1305 of FIG. 13). A PTG functionality model predicts the same effect with our model, observing a slower incline if phosphate is elevated only slightly over time (see, for example, graphs 1405 and 1410 of FIG. 14).

Predictions generated with PTG functionality models according to some embodiments agree with observed PTH response and PTG adaptation in a number of acute and chronic alterations of Ca2+, P, and 1,25D. The PTG functionality models accurately account for adaptation mechanisms such as decreased intracellular PTH degradation, PTH production rate, and elevated PTG proliferation rate. More importantly, PTG functionality models fully capture the different time scales these mechanisms are acting on. In some embodiments, a driving force of the PTG functionality models is the description of changes in the CaSR which is the crucial regulator of the PTG. The PTG functionality models were validated via comparing its predictions with published experimental data under different conditions. The model predictions agree with observations in all analyzed scenarios, for instance, different rates of induced hypocalcemia, hysteresis, hyperplasia in the case of induced chronic mild hypocalcemia, and secondary hyperparathyroidism in the case of chronically elevated serum phosphate levels as well as chronically low 1,25DH levels. These features make PTG functionality models useful in patients suffering from secondary hyperparathyroidism, such as those with CKD or on dialysis.

In some embodiments, PTG functionality models may include all of the known adaptive mechanisms which regulate the CaSR. The predictions are based on positive and negative feedback systems acting on the CaSR. The effect of therapeutic interventions acting on the CaSR, such as the calcimimetic drugs cinacalcet or etelcalcetide (for example, via a calcimimetic model according to some embodiments) may be incorporated by using an operational model of allosterism on the CaSR. For example, a calcimimetic model according to some embodiments may include a pharmacokinetic model that may be easily incorporated in all other models by using an operational model of allosterims which transfers the actual ionized calcium concentration by the amount of free drug in the plasma. For instance, allosterims may be as described in Leach et al., "Towards a structural understanding of allosteric drugs at the human calcium-sensing receptor," *Cell Research* 26:574-592, 2016; Leach et al., "Molecular Mechanisms of Action and In Vivo Validation of an M-4 Muscarinic Acetylcholine Receptor Allosteric Modulator with Potential Antipsychotic Properties," *Neuropsychopharmacology* 35:855-869, 2010; Leach et al., "Allosteric GPCR modulators: taking advantage of permissive receptor pharmacology," *Trends in Pharmacological Sciences* 28:382-389, 2007; and/or Padhi D and Harris R, "Clinical Pharmacokinetic and Pharmacodynamic Profile of Cinacalcet Hydrochloride," *Clinical Pharmacokinetics* 48:303-311, 2009.

Accordingly, PTG functionality models may operate to, inter alia, provide a complementary tool to study treatment strategies, like combinations of calcimimetics and vitamin D analogs. The only input variables are the key regulators of PTG cells in hemodialysis patients, i.e. calcium, 1,25D, and phosphate. Therefore, PTG functionality models can be combined with a bone model, allowing the analysis of a highly complex system involving a cascade of regulatory triggers and feedback loops.

Although PTG functionality models simulated situations of patients with total loss of the kidney function as a system regulator, the model is more generally applicable to other patients groups, for example, patients suffering from primary hyperparatyroidism. For example, the only parameter which is directly influenced by the kidney function is the clearance rate, $k_{cl}$. Since PTH is cleared by the liver the kidney the clearance rate is higher in healthy subjects (see, for example, Table 505 of FIG. 5) or CKD patients with residual kidney function. For long term simulations, the clearance rate may be assumed to be reduced by a factor 2 in some embodiments.

Case Study II: Calcimimetic Model Simulation

The executive summary of the 2017 KDIGO Chronic Kidney Disease-Mineral and Bone Disorder (CKD-MBD) Guideline Update recommends to maintain PTH within 14 pmol/L and 62 pmol/L. One strategy to reach this goal is to target the CaSR. Calcimimetics like cinacalcet or etelcalcetide enhance the interaction between the ionized calcium concentration (Ca2+) and the CaSR by allosteric activation. The higher sensitivity of the CaSR to Ca2+ leads to an inverse relationship between plasma PTH and cinacalcet concentrations. PTH concentration declines after the administration of cinacalcet until it reaches a minimum approximately 2-3 hours after dosing.

Cinacalcet hydrochloride is widely used in hemodialysis patients. Following oral administration, the plasma concentration peaks within 2-6 hours. The absolute bioavailability is only between 20-25% while absorption is close to 100% indicating a high first-pass metabolism. Since almost 95% of the drug in the plasma is protein bound, the pharmacokinetics is not altered by hemodialysis.

Due to the vast clinical use of cinacalcet, a realistic model of CKD-MBD may feature the use of cinacalcet and its effects. To be of clinical use, the cinacalcet model should be readily adaptable to various conditions, such as hepatic impairment enhancing cinacalcet exposure. Moreover, it should be able to reflect different administration scenarios including patient adherence which is known to be poor, supposedly due to gastrointestinal side effects and high pill load.

Accordingly, some embodiments may use a multi-compartment calcimimetic model based on physiological considerations capturing all major pharmacokinetics parameters of cinacalcet, for example, as depicted, at least in part, in FIG. 2B. Case Study II may use a calcimimetic model with less than six compartments, for instance, a five-compartment model that does not include a slow tissue compartment may be used. Moreover, a calcimimetic model according to some embodiments may provide an intuitive individualization to various conditions or administration regiments and omit any numerical instabilities in order to be easily implemented in other physiological models.

Figure 15:
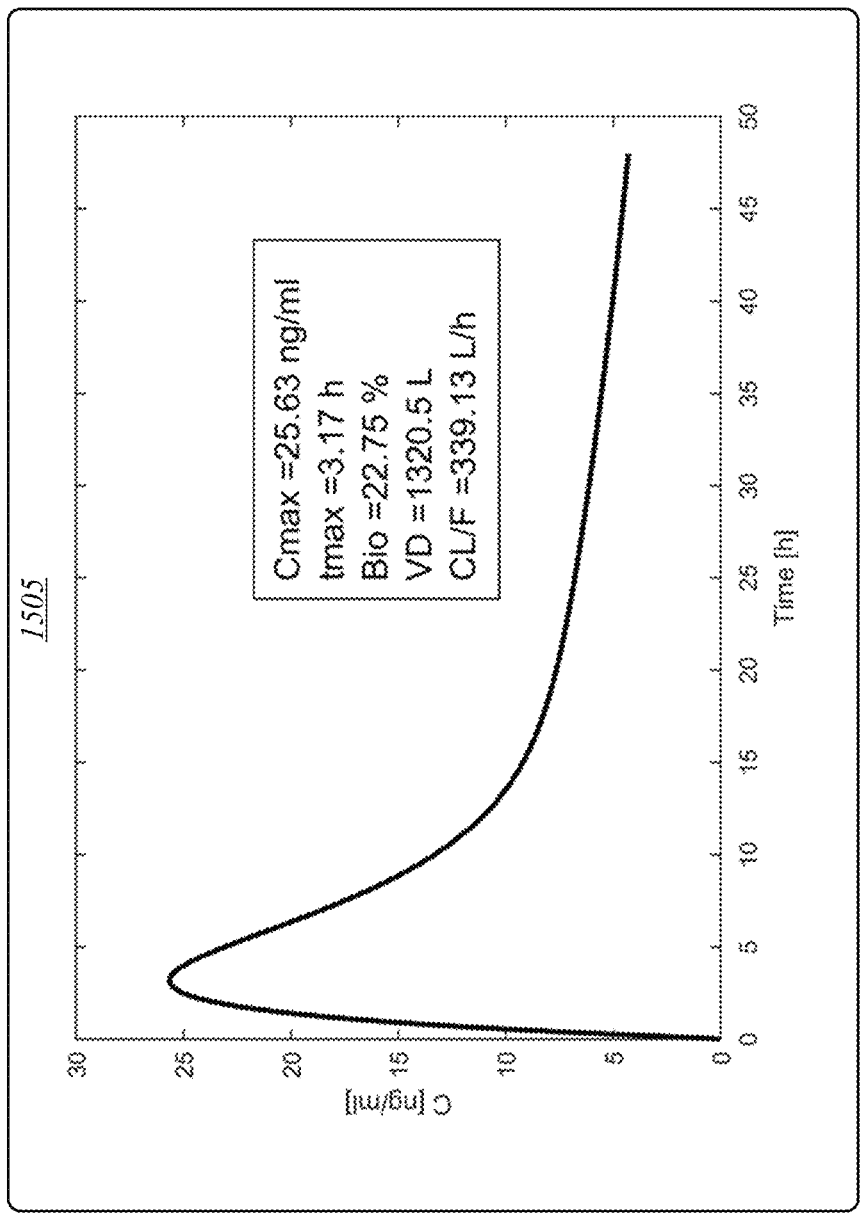
FIG. 15 depicts a graph of time versus cinacalcet (C) concentrations in accordance with the present disclosure.
Figure 16:
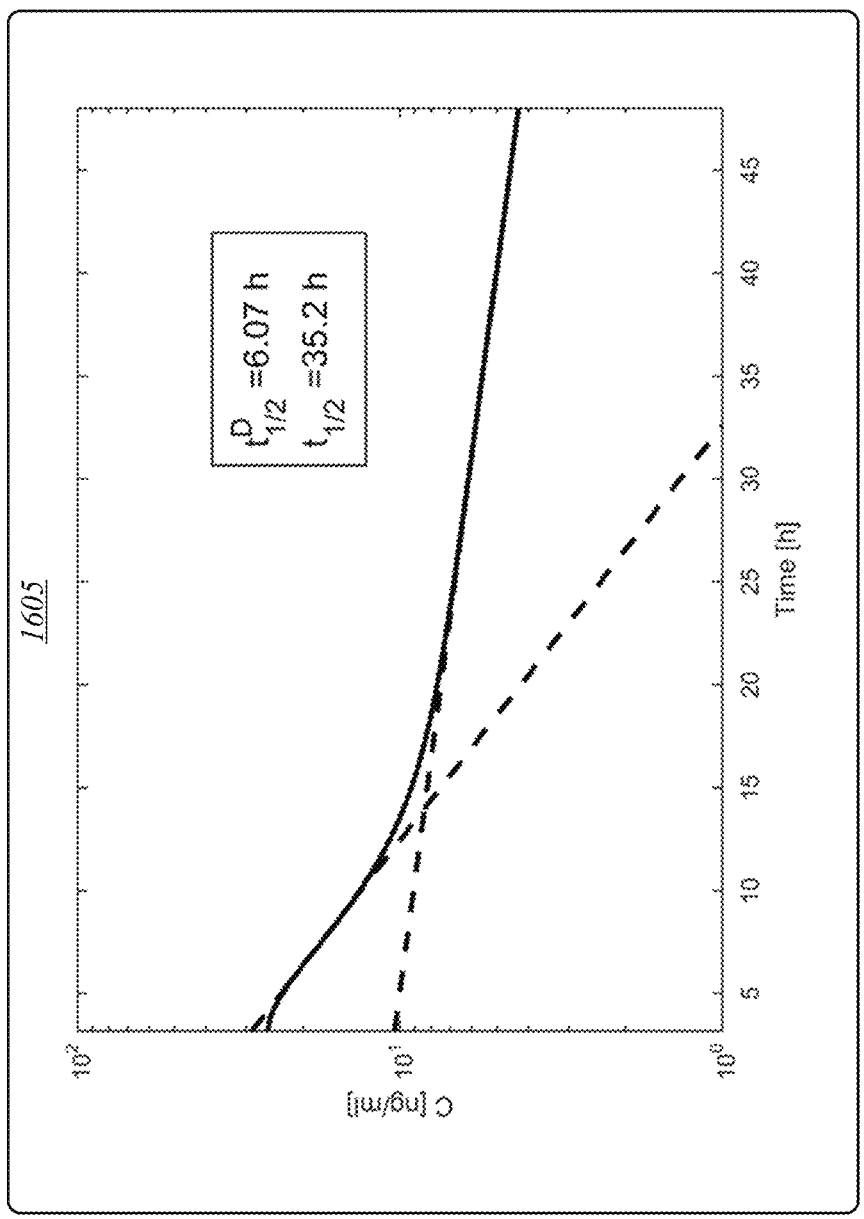
FIG. 16 depicts a graph of time versus cinacalcet (C) concentrations in accordance with the present disclosure.
Figure 17:
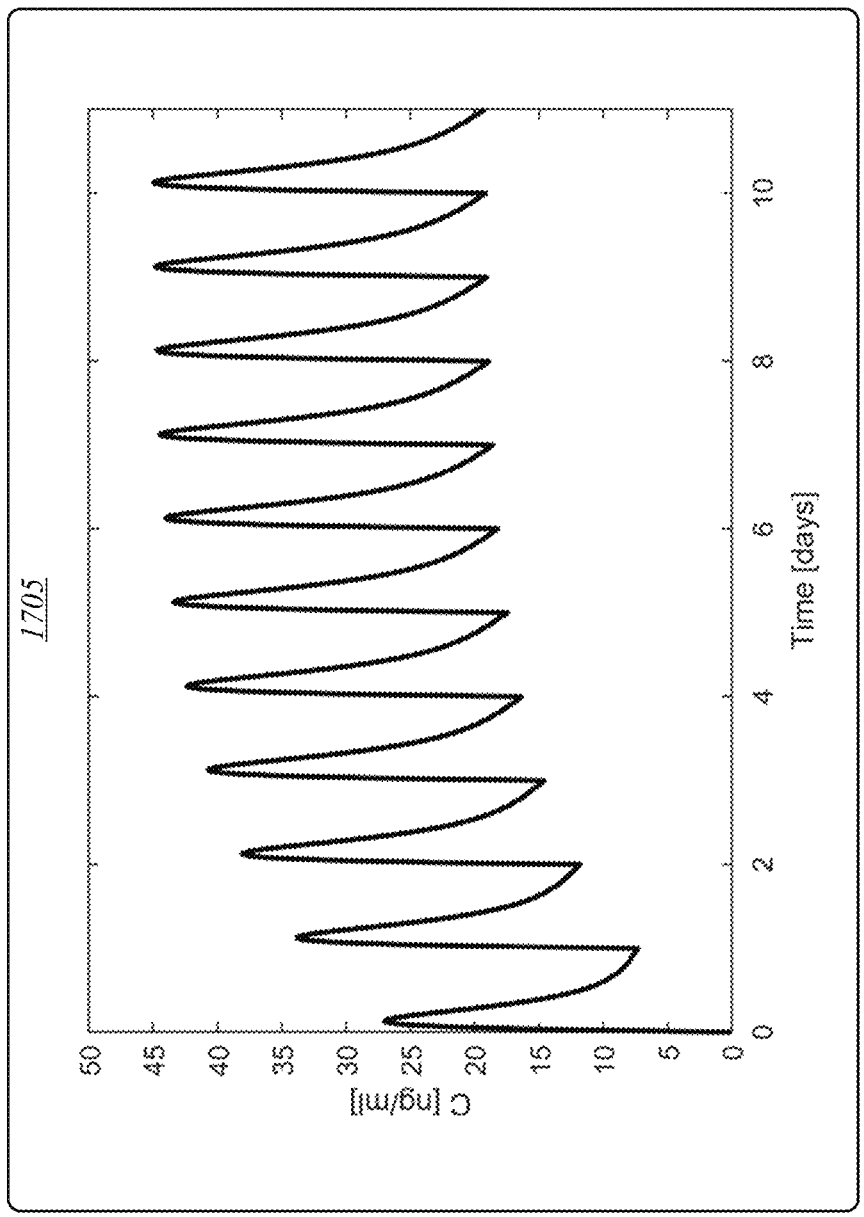
FIG. 17 depicts a graph of time versus cinacalcet (C) concentrations in accordance with the present disclosure.

The simulated pharmacokinetics profile of a single oral administration based on the proposed six-compartment model is shown in graph 1505 of FIG. 15 and graph 1605 of FIG. 16. FIG. 15 depicts graph 1505 of cinancelet concentration versus time after a single 75 mg dose. The mean reference values for $C_{max}$ is 26.6 ng/mL (9.4 SD), the reference range for $t_{max}$ is 1-6 hours, for Bio 20-25%, and for VD 1000-1250 L. Mean apparent oral clearance rate is CL/F is 314 L/h (148 SD). FIG. 16 depicts graph 1505 of cinancelet concentration versus time after a single 75 mg dose (solid line) and the exponential fits used for half-life estimation (dotted lines) on a logarithmic scale. The reference value for the half-life of distribution $t_{1/2}^D$ is 6 hours, the reference range for the terminal half-life is 30-40 hours. In general, the results are qualitatively and quantitatively in close agreement with established clinical data. The simulations of daily administration of cinacalcet at 75 mg every 24 hours predict a steady state within seven days (see, for example, graph 1705 of FIG. 17) in accordance with known clinical data. A calcimimetic model may be configured to capture all seven key pharmacokinetic parameters (i.e. $C_{max}$, $t_{max}$, Bio, CL/F, $t_{1/2}$, $t_{1/2}^D$, and VD) simultaneously, while a linear mass-balance may not be able to.

Figure 18:
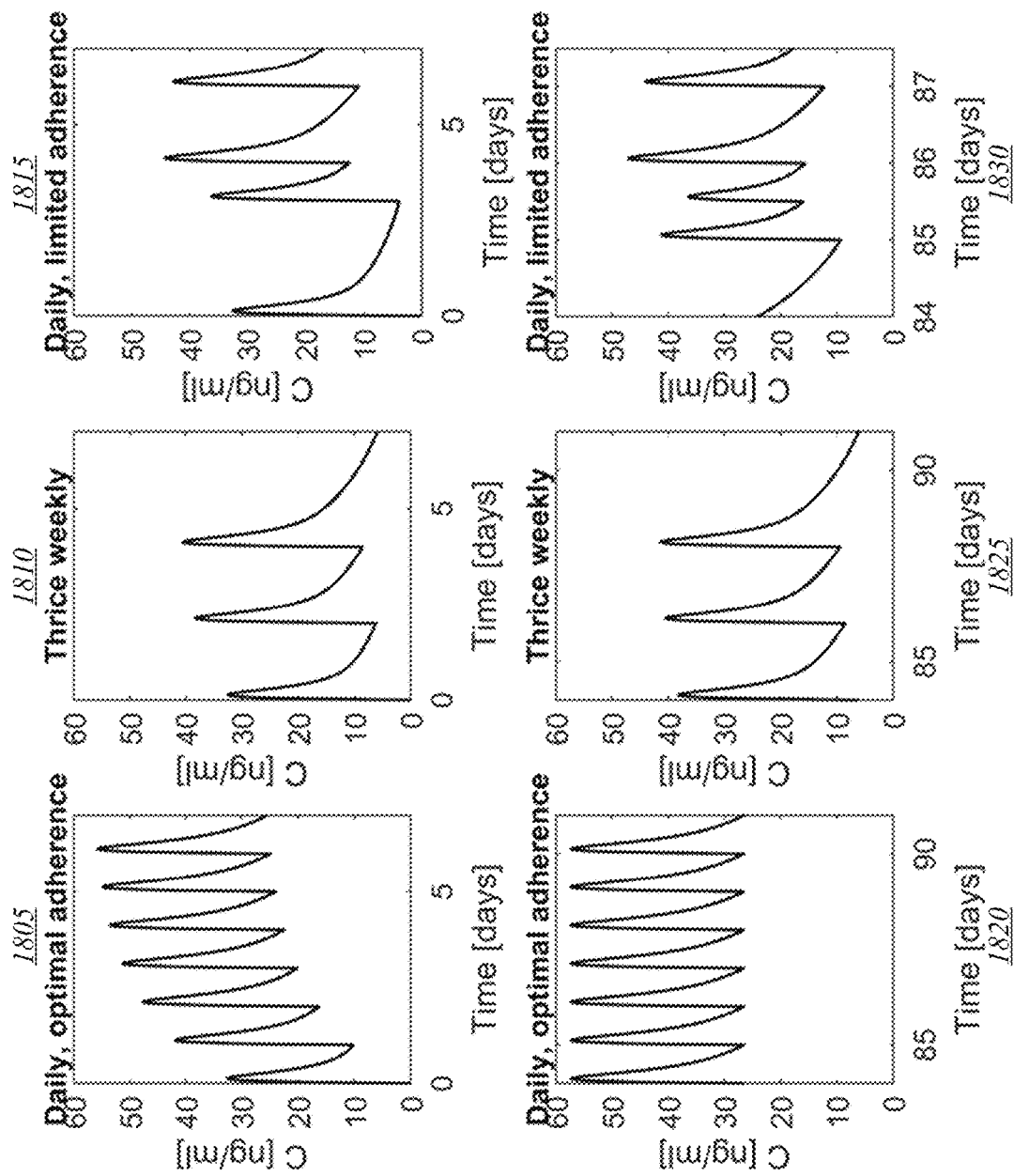
FIG. 18 depicts graphs of time versus cinacalcet (C) concentrations for various dosing regimens in accordance with the present disclosure.

To assess the impact of dosing regiments on the total exposure Clinical Study II analyzed the weekly average cinacalcet concentration (for instance, at each time point) in the blood for three different dosing regiments: daily administration, administration three times a week, and administration with a realistic patient refill rate of 64%. For the realistic patient refill rate random days without administration were selected. The results are presented in graphs 1805, 1810, 1815, 1820, 1825, and 1830 of FIG. 18.

The linear multi-compartment calcimimetic model may be used to describe the complex pharmacokinetic behavior of cinacalcet in the human body. Such an approach may allow the analysis of the effect of different dosing regiments on the drug concentration in the body that could otherwise only be addresses by clinical studies. The analysis can help to evaluate dose titration schemes and administration schemes. One non-limiting technological advantage of calcimimetic models according to some embodiments is its linear structure allowing long term predictions which are numerically stable and fast. Due to the physiological meaningful compartments, adjustments to conditions like hepatic impairment are straight forward. Combined with a model for the parathyroid gland and bone metabolism, calcimimetic models according to some embodiments may provide a ready to use tool for clinical trial simulations to explore effects of relevant factors, such as patient adherence, off-label administration regiments, the effect of administration with food, and/or the like.

The low bio-availability of 20-25% indicates a high first pass metabolism. Hepatic impairment results in higher terminal half-life values (40-70% for moderate to severe impairment) and higher total exposure (2.4 old to 4.2-fold higher in patients with moderate to severe impairment). Administration with food results in higher bio-availability and consequently higher peak concentrations and total exposure values. Around 95% of the drug is protein bound. Therefore, the effect of HD on the pharmacokinetics is negligible. The high volume of distribution at steady state of 1000 liters indicates a vast distribution outside the systemic circulation. Experiments with radioactive labeled cinacalcet have shown that the drug peaks at different times in different tissues. Roughly, tissue can be lumped into two groups: one group with smaller time to peak and one group with large time to peak operating like a buffer for cinacalcet.

An illustrative calcimimetic model is depicted in FIG. 3A, using six physiological motivated compartments, for example, compartments for absorption, first pass metabolism, plasma free drug, and protein bound as well as two tissue compartments. Constant rate functions are used between the compartments. The amount of drug in each compartment can be calculated by solving the following system of linear ordinary differential equations:

$$\frac{d\vec{y}}{dt} = A \cdot \vec{y}, \quad (21)$$

where $\vec{y}_1$ corresponds to the amount of drug in the absorption compartment, $\vec{y}_2$ to the amount of drug in the first pass metabolism, $\vec{y}_3$ and $\vec{y}_4$ to the amount of drug in the free and protein bound plasma compartments. $\vec{y}_5$ and $\vec{y}_6$ correspond to the amount of drug in the fast and slow tissue, respectively. The initial dose is delivered to the absorption compartment. In cinacalcet naive patients, the initial condition is given by the vector $\vec{y}_0$=(Administered dose, 0, 0, 0, 0, 0). In non-naive patients the condition for a drug administration at time $t_a$ is $\vec{y}_{t_a}$=($t_a$)+$\vec{y}_0$. The coefficient matrix A may be written as:

$$A = \begin{pmatrix} -k_a & 0 & 0 & 0 & 0 & 0 \\ k_a & -k_e - k_{lp} & 0 & 0 & 0 & 0 \\ 0 & k_{lp} & -k_a - k_{PTj} - k_{PTs} - k_e^P & k_f & k_{TPf} & k_{TPs} \\ 0 & 0 & k_b & -k_f & 0 & 0 \\ 0 & 0 & k_{PTf} & 0 & -k_{TPf} & 0 \\ 0 & 0 & k_{PTs} & 0 & 0 & -k_{TPs} \end{pmatrix}.$$

Removal of a compartment from the calcimimetic model from matrix A may involve removing corresponding columns and/or rows from the matrix. For example, to remove the slow tissue compartment, the last (or bottom-most) row and the last (or right-most) column may be removed to generate the following coefficient matrix A for a five-compartment model:

$$A = \begin{pmatrix} -k_a & 0 & 0 & 0 & 0 \\ k_a & -k_e - k_{lp} & 0 & 0 & 0 \\ 0 & k_{lp} & -k_a - k_{PTj} - k_{PTs} - k_e^P & k_f & k_{TPf} \\ 0 & 0 & k_b & -k_f & 0 \\ 0 & 0 & k_{PTf} & 0 & -k_{TPf} \end{pmatrix}.$$

This linear system has the distinct advantage that it can be solved by solving the corresponding eigenvalue problem, for example, if $\lambda 1, \ldots, \lambda 6$ are the distinct eigenvalues of A and $\Phi = (\vec{v}_1, \ldots, \vec{v}_6)$ is a matrix containing the corresponding eigenvectors, then the solution of the differential equation with the last dose administration at time $t_a$ is:

$$\vec{y}(t) = \sum_{l=1}^{6} (\Phi^{-1} \vec{y}_{t_a}) j \vec{v} j e^{\lambda_j t}, \; t \geq t_a. \quad (22)$$

Therefore, at any given time t, the drug amount can be calculated by evaluating the amount of drug in all compartments only for the preceding administration times. Long time simulations are therefore very fast and numerically stable.

Known data may be used to estimate the coefficient matrix A. The natural constriction is that all eigenvalues should be distinct and negative to ensure the convergence to zero in all compartments in the absence of further drug administrations. An average plasma volume of 3 liters may be assumed and a single oral dose of 75 mg cinacalcet may be assumed. The target maximum plasma concentration $C_{max}$ should be close to 26.8 ng/mL, the time until the maximum plasma concentration is reached around 2.3 hours, terminal half-life $t_{1/2}$ 30-4 hours, distribution half-life $t_D$ 6 hours. The apparent oral clearance rate CL/F, is defined as:

$$CL/F = \frac{(\text{administered dose})}{\int_0^\infty C(\tau)d\tau} \quad (23)$$

which should be around 314 L/h. The apparent volume of distribution at steady state $V_D$, defined as:

$$V_D = (\text{administered dose}) \cdot \frac{\int_0^\infty t \cdot C(t)dt}{\left(\int_0^\infty C(t)dt\right)^2} \quad (24)$$

which should be around 1000 L. Finally, the bioavailability Bio should be between 20 and 25% for fasting patients. The bioavailability may be determined as:

$$Bio = \frac{\int_0^\infty C_{oral}(t)dt}{\int_0^\infty C_{iv}(t)dt}, \quad (25)$$

where $C_{iv}$ is the plasma concentration of the intravenously administered drug. $C_{iv}$ may be calculated by analyzing the model modified for intravenous bolus injection. The drug may be administered to the "plasma free drug" compartment thereby omitting the absorption and first pass metabolism compartments. $C_{oral}$ is the plasma concentration of the orally administered drug.

Typical model parameters are given in table 1905 of FIG. 19. In some embodiments, $k_f$ may be set to 0.0526 $k_b$ to ensure that 95% of the drug is protein bound in the steady state. For simulations regarding food intake, the absorption rate may be slightly enhanced to $k_a$=0.6 h$^{-1}$ in order to accommodate a slightly lower $t_{max}$, and first pass metabolism rate $k_e$ may be reduced to 0.13 h$^{-1}$.

A sensitivity analysis was conducted to study the impact of uncertainties in for all parameters in the coefficient matrix A. The base values of each of these parameters was either divided or multiplied by a factor of 2. The respective pharmacokinetic parameters were calculated assuming a single dose administration of 60 mg cinacalcet. These values were compared to the corresponding base case values and the results generated as depicted in table 2005 of FIG. 20. The analysis reveals, among other things, that $C_x$ is most sensitive to changes of $k_e$, $k_{lp}$ and $k_{PT\,f}$. Bio-availability is most sensitive to changes of $k_e$ and $k_{lp}$. Due to the buffer function of the tissue compartments the terminal half-life is most sensitive to changes of $k_{PT\,f}$, $k_{PT\,s}$ and $k_{PT\,s}$. The half-life of distribution as well as $t_{max}$ are sensitive to changes in $k_b$ and $k_e$. Due to its definition the apparent oral clearance rate CL/F is sensitive to changes in $j_e$ and $k_{lp}$.

Figure 21:
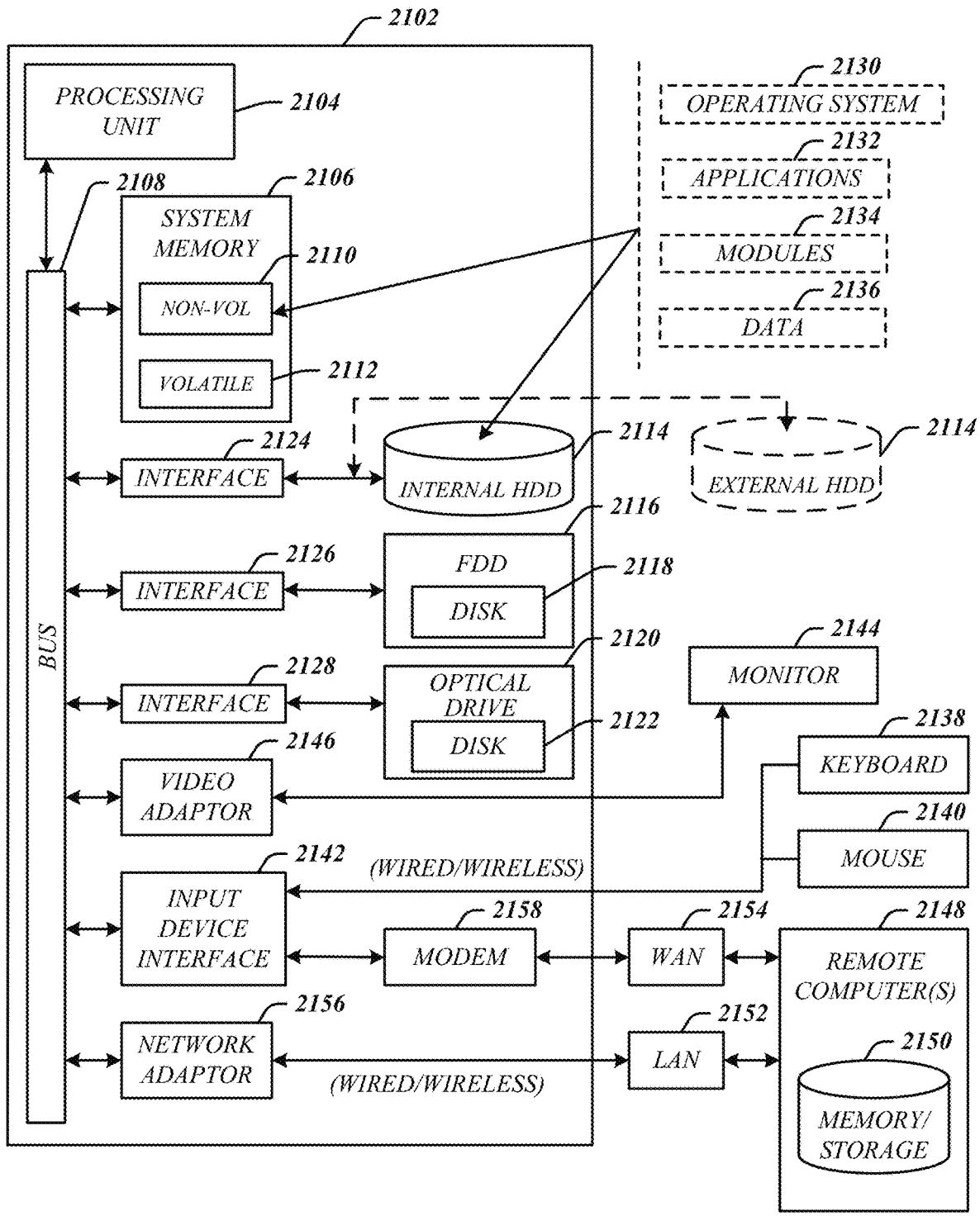
FIG. 21 illustrates an embodiment of a computing architecture in accordance with the present disclosure.

FIG. 21 illustrates an embodiment of an exemplary computing architecture 2100 suitable for implementing various embodiments as previously described. In various embodiments, the computing architecture 2100 may comprise or be implemented as part of an electronic device. In some embodiments, the computing architecture 2100 may be representative, for example, of computing device 110. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 2100. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 2100 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 2100.

As shown in FIG. 21, the computing architecture 2100 comprises a processing unit 2104, a system memory 2106 and a system bus 2108. The processing unit 2104 may be a commercially available processor and may include dual microprocessors, multi-core processors, and other multi-processor architectures.

The system bus 2108 provides an interface for system components including, but not limited to, the system memory 2106 to the processing unit 2104. The system bus 2108 can be any of several types of bus structure that may further interconnect to a memory bus (with or without a memory controller), a peripheral bus, and a local bus using any of a variety of commercially available bus architectures. Interface adapters may connect to the system bus 2108 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 2106 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 21, the system memory 2106 can include non-volatile memory 2110 and/or volatile memory 2112. A basic input/output system (BIOS) can be stored in the non-volatile memory 2110. The computer 2102 may include various types of computer-readable storage media in the form of one or more lower speed memory units, including an internal (or external) hard disk drive (HDD) 2114, a magnetic floppy disk drive (FDD) 2116 to read from or write to a removable magnetic disk 2111, and an optical disk drive 2120 to read from or write to a removable optical disk 2122 (e.g., a CD-ROM or DVD). The HDD 2114, FDD 2116 and optical disk drive 2120 can be connected to the system bus 2108 by a HDD interface 2124, an FDD interface 2126 and an optical drive interface 2128, respectively. The HDD interface 2124 for external drive implementations can include at least one or both of Universal Serial Bus (USB) and IEEE 1114 interface technologies.

The drives and associated computer-readable media provide volatile and/or nonvolatile storage of data, data structures, computer-executable instructions, and so forth. For example, a number of program modules can be stored in the drives and memory units 2110, 2112, including an operating system 2130, one or more application programs 2132, other program modules 2134, and program data 2136. In one embodiment, the one or more application programs 2132, other program modules 2134, and program data 2136 can include, for example, the various applications and/or components of computing device 110.

A user can enter commands and information into the computer 2102 through one or more wired/wireless input devices, for example, a keyboard 2138 and a pointing device, such as a mouse 2140. These and other input devices are often connected to the processing unit 2104 through an input device interface 2142 that is coupled to the system bus 2108, but can be connected by other interfaces.

A monitor 2144 or other type of display device is also connected to the system bus 2108 via an interface, such as a video adaptor 2146. The monitor 2144 may be internal or external to the computer 2102. In addition to the monitor 2144, a computer typically includes other peripheral output devices, such as speakers, printers, and so forth.

The computer 2102 may operate in a networked environment using logical connections via wired and/or wireless communications to one or more remote computers, such as a remote computer 2148. The remote computer 2148 can be a workstation, a server computer, a router, a personal computer, portable computer, microprocessor-based entertainment appliance, a peer device or other common network node, and typically includes many or all of the elements described relative to the computer 2102, although, for purposes of brevity, only a memory/storage device 2150 is illustrated. The logical connections depicted include wired/wireless connectivity to a local area network (LAN) 2152 and/or larger networks, for example, a wide area network (WAN) 2154. Such LAN and WAN networking environments are commonplace in offices and companies, and facilitate enterprise-wide computer networks, such as intranets, all of which may connect to a global communications network, for example, the Internet.

The computer 2102 is operable to communicate with wired and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A computer-implemented method of virtual parathyroid gland (PTG) functionality analysis, the method comprising, via a processor of a computing device:
   providing a PTG functionality model configured to simulate a functionality of a PTG of a patient with at least one health abnormality affecting PTG function, the model operative to:
     receive a plurality of parameters configured to regulate activity of calcium-sensing receptors (CaSR), the plurality of parameters comprising a calcium concentration, a vitamin D concentration, and a phosphorous concentration,
     simulate CaSR expression and vitamin D receptor (VDR) expression via:
       a positive feedback loop between the CaSR expression and the VDR expression, and
       suppression of the CaSR expression and the VDR expression by phosphate,
     initiate at least one PTG adaptation based on the plurality of parameters, and
     determine a model output comprising a parathyroid hormone (PTH) concentration at one or more time intervals.

2. The computer-implemented method of claim 1, the at least one health abnormality comprising one of chronic kidney disease (CKD), hypoparathyroidism, hyperparathyroidism, hypocalcemia, hypercalcemia or hyperphosphatemia.

3. The computer-implemented method of claim 1, the model operative to down-regulate at last one of a PTH release rate, a production rate, or a proliferation rate responsive to the calcium concentration, the vitamin D concentration, and the phosphorous concentration being within an optimal range.

4. The computer-implemented method of claim 1, the model operative to initiate the at least one PTG adaptation responsive to one of the plurality of parameters being outside of an optimal range for a critical time period.

5. The computer-implemented method of claim 1, the calcium concentration comprising one of ionized calcium ($Ca^{2+}$) or a calcimimetic concentration determined via a calcimimetic model.

6. The computer-implemented method of claim 4, the model operative to use at least one stimulus function to facilitate the at least one PTG adaptation responsive to a deviation from the optimal range for one of the plurality of parameters.

7. The computer-implemented method of claim 1, CaSR expression and VDR expression are determined based on the following:

$$\frac{dCaSR}{dt} = p_{Ca} \cdot (Ca^{in} + (VDR - 1) - P^{in}) \cdot CaSR + n_{Ca} \cdot (1 - CaSR), \quad (1)$$

$$\frac{dVDR}{dt} = p_D \cdot (D^{in} + (CaSR - 1) - P^{in}) \cdot VDR + n_D \cdot (1 - VDR), \quad (2)$$

$$\frac{dCa^{in}}{dt} = \qquad (3)$$
$$(stim_C(CS - Ca_{opt}) \cdot (1 - \text{sign}(stim_C(CS - Ca_{opt}))Ca^{in}) - Ca^{in}) \cdot \tau_C,$$

$$\frac{dD^{in}}{dt} = (stim_D(DS - D_{opt}) \cdot (1 - \text{sign}(stim_D(DS - D_{opt}))D^{in}) - D^{in}) \cdot \tau_D, \quad (4)$$

$$\frac{dP^{in}}{dt} = (stim_P(P - P_{opt}) \cdot (1 - \text{sign}(stim_P(P - P_{opt}))P^{in}) - P^{in}) \cdot \tau_P, \quad (5)$$

wherein $Ca_{opt}$ comprises an optimal blood value for calcium, $D_{opt}$ comprises an optimal blood value for vitamin D, $P_{opt}$ comprises an optimal blood value for phosphate, P comprises a serum phosphate concentration, wherein $p_{Ca}$ and $n_{Ca}$ are intensity parameters for Ca, wherein $p_D$ and $n_D$ are intensity parameters for vitamin D, wherein $Cd^{in}$, $D^{in}$ and $P^{in}$ are factors determining an effect of the stimulus on the CaSR expression and VDR expression, wherein $\tau_C$, $\tau_D$, and $\tau_p$ are time constants operative to determine a convergence rate to a steady state after a step-wise change in the calcium concentration, vitamin D concentration, or phosphate concentration.

8. The computer-implemented method of claim 1, the PTG functionality model to determine a sensed calcium concentration (CS) according to the following:

$$\frac{dCS}{dt} = sens(CaSR + VDR)C - CS, \quad (6)$$

$$\frac{dDS}{dt} = sens(CaSR + VDR)D - DS, \quad (7)$$

$$sens(x) = A_S + (1 - A_S) \cdot (x/2), \quad (8)$$

where C is the calcium concentration and D is the vitamin D concentration,
where DS is a sensed vitamin D concentration,
where $A_s$ is a maximal rate of decay.

9. The computer-implemented method of claim 1, comprising determining at least one treatment recommendation based on the model output.

10. A computer-implemented method of virtual parathyroid gland (PTG) functionality analysis, the method comprising, via a processor of a computing device:
provided a calcimimetic model configured to simulate administration of a calcimimetic compound to a patient with at least one health abnormality affecting PTG function, the calcimimetic model operative to:
receive a calcimimetic dose,
determine a concentration of the calcimimetic compound in at least one of a plurality of physiological compartments, each of the plurality of physiological compartments related to an adjacent physiological compartment via at least one constant rate function, and
determine an output of a total calcimimetic concentration for at least one time period.

11. The computer-implemented method of claim 10, the calcimimetic compound comprising cinacalcet.

12. The computer-implemented method of claim 10, the plurality of physiological compartments comprising an absorption compartment, a first pass metabolism compartment, a plasma free drug compartment, a plasma protein bound compartment, a fast tissue compartment, and a slow tissue compartment.

13. The computer-implemented method of claim 12, the absorption compartment arranged adjacent to the first pass metabolism compartment and related via a constant rate function.

14. The computer-implemented method of claim 10, the calcimimetic model operative to determine a plurality of pharmacokinetic parameters simultaneously, the plurality of pharmacokinetic parameters comprising $C_{max}$, $t_{max}$, Bio, CL/F, $t_{1/2}$, $t_{1/2}^D$, and VD,
where $C_{max}$ is a maximum plasma concentration, $t_{max}$ is a time to reach $C_{max}$, Bio is a bioavailability, CL/F is an apparent oral clearance rate, $t_{1/2}$ is a terminal half-life, $t_{1/2}^D$, is a distribution half-life, and VD is a volume of distribution.

15. The computer-implemented method of claim 10, the output provided as a calcium concentration input of a PTG functionality model.

16. The computer-implemented method of claim 10, the output provided as a calcium concentration input of a PTG functionality model via an operational model of allosterims configured to transfer the calcium concentration based on an amount of free drug in plasma.

17. The computer-implemented method of claim 10, the calcimimetic model operative to determine an amount of the calcimimetic compound in each of the plurality of physiological compartments based on the following:

$$\frac{d\vec{y}}{dt} = A \cdot \vec{y}.$$

wherein $\vec{y}$ corresponds to the amount of the calcimimetic compound in one of the plurality of physiological compartments and A is a coefficient matrix for the plurality of physiological compartments.

18. The computer-implemented method of claim 17, wherein the calcimimetic compound in each of the plurality of physiological compartment is determined for $\vec{y}_1$-$\vec{y}_5$, wherein $\vec{y}_1$ corresponds to the amount of the calcimimetic compound in the absorption compartment, $\vec{y}_2$ corresponds to the amount of the calcimimetic compound in the first pass metabolism compartment, $\vec{y}_3$ corresponds to the amount of the calcimimetic compound in the plasma free drug compartment, $\vec{y}_4$ corresponds to the amount of the calcimimetic compound in the plasma protein bound compartment, $\vec{y}_5$ corresponds to the amount of the calcimimetic compound in the fast tissue compartment.

* * * * *